(12) United States Patent
Van Der Zouw et al.

(10) Patent No.: US 9,753,296 B2
(45) Date of Patent: Sep. 5, 2017

(54) ILLUMINATION SYSTEM, INSPECTION APPARATUS INCLUDING SUCH AN ILLUMINATION SYSTEM, INSPECTION METHOD AND MANUFACTURING METHOD

(71) Applicant: ASML Netherlands B.V., Veldhoven (NL)

(72) Inventors: Gerbrand Van Der Zouw, Waalre (NL); Martin Jacobus Johan Jak, 's-Hertogenbosch (NL); Martin Ebert, Valkenswaard (NL)

(73) Assignee: ASML Netherlands B.V., Veldhoven (NL)

( * ) Notice: Subject to any disclaimer, the term of this patent is extended or adjusted under 35 U.S.C. 154(b) by 125 days.

(21) Appl. No.: 14/805,402

(22) Filed: Jul. 21, 2015

(65) Prior Publication Data

US 2016/0025992 A1    Jan. 28, 2016

(30) Foreign Application Priority Data

Jul. 28, 2014  (EP) ..................................... 14178791
Nov. 5, 2014  (EP) ..................................... 14191958

(51) Int. Cl.
*G01N 21/00*       (2006.01)
*G02B 27/28*       (2006.01)
(Continued)

(52) U.S. Cl.
CPC .............. *G02B 27/283* (2013.01); *G01J 1/08* (2013.01); *G01N 21/8806* (2013.01);
(Continued)

(58) Field of Classification Search
CPC ............. G03F 7/70275; G03F 7/70058; G03F 7/70208; G01N 21/4738; G01N 21/8806;
(Continued)

(56) References Cited

U.S. PATENT DOCUMENTS 5,229,872 A    7/1993    Mumola
5,801,798 A    9/1998    Chen et al.
(Continued)

FOREIGN PATENT DOCUMENTS

GB          2405544 A       3/2005
WO     WO 2008/052405 A1    5/2008
WO     WO 2013/178422 A1   12/2013

OTHER PUBLICATIONS

International Search Report directed to related International Patent Application No. PCT/EP2015/065984, mailed Sep. 11, 2015; 3 pages.

(Continued)

*Primary Examiner* — Hoa Pham
(74) *Attorney, Agent, or Firm* — Sterne, Kessler, Goldstein & Fox P.L.L.C.

(57) ABSTRACT

In an illumination system (12, 13) for a scatterometer, first and second spatial light modulators lie in a common plane and are formed by different portions of a single liquid crystal cell (260). Pre-polarizers (250) apply polarization to first and second radiation prior to the spatial light modulators. A first spatial light modulator (236-S) varies a polarization state of the first radiation in accordance with a first programmable pattern. Second spatial light modulator (236-P) varies a polarization state of the second radiation accordance with a second programmable pattern. A polarizing beam splitter (234) selectively transmits each of the spatially modulated first and second radiation to a common output path, depending on the polarization state of the radiation. In an embodiment, functions of pre-polarizers are performed by the polarizing beam splitter.

20 Claims, 13 Drawing Sheets

(51) Int. Cl.
*G02F 1/01* (2006.01)
*G01J 1/08* (2006.01)
*G01N 21/88* (2006.01)
*G01N 21/95* (2006.01)
*G03F 7/20* (2006.01)

(52) U.S. Cl.
CPC ........... *G01N 21/9501* (2013.01); *G02F 1/01* (2013.01); *G03F 7/70633* (2013.01); *G01N 2021/8848* (2013.01); *G01N 2201/0675* (2013.01)

(58) Field of Classification Search
CPC ..... G01N 2201/0675; G01N 2201/112; G01N 2201/061; G01N 2201/0636; G02B 27/0043; G02B 27/10
USPC ....... 356/369, 237.1–237.5, 121; 355/67, 71, 355/53
See application file for complete search history.

(56) References Cited

U.S. PATENT DOCUMENTS

| | | | |
|---|---|---|---|
| 5,801,799 A | 9/1998 | Chen et al. | |
| 6,407,766 B1* | 6/2002 | Ramanujan | B41J 2/465 347/239 |
| 8,379,187 B2* | 2/2013 | Tanitsu | G02B 27/0927 355/67 |
| 9,140,998 B2* | 9/2015 | Smilde | G03F 7/70483 |
| 2004/0033426 A1 | 2/2004 | Den Boef et al. | |
| 2005/0018179 A1 | 1/2005 | Bevis et al. | |
| 2005/0128457 A1* | 6/2005 | Nishimura | G03F 7/70466 355/67 |
| 2005/0140949 A1* | 6/2005 | Jasper | G03F 1/62 355/53 |
| 2005/0286035 A1* | 12/2005 | Troost | G03F 7/70225 355/67 |
| 2006/0033921 A1 | 2/2006 | Den Boef et al. | |
| 2006/0066855 A1 | 3/2006 | Boef et al. | |
| 2006/0109463 A1 | 5/2006 | Boef et al. | |
| 2007/0091325 A1 | 4/2007 | Nikoonahad | |
| 2007/0273798 A1* | 11/2007 | Silverstein | G02B 13/22 348/752 |
| 2007/0279630 A1 | 12/2007 | Kandel et al. | |
| 2007/0284547 A1 | 12/2007 | Sejersen et al. | |
| 2008/0137099 A1 | 6/2008 | Hugers | |
| 2008/0304030 A1 | 12/2008 | Lous | |
| 2009/0109417 A1* | 4/2009 | Tanitsu | G02B 27/0927 355/67 |
| 2010/0201963 A1 | 8/2010 | Cramer et al. | |
| 2010/0328655 A1 | 12/2010 | Den Boef | |
| 2011/0027704 A1 | 2/2011 | Cramer et al. | |
| 2011/0043791 A1 | 2/2011 | Smilde et al. | |
| 2011/0069292 A1 | 3/2011 | Den Boef | |
| 2011/0102753 A1 | 5/2011 | Van De Kerkhof et al. | |
| 2012/0038929 A1 | 2/2012 | Den Boef et al. | |
| 2012/0044470 A1 | 2/2012 | Smilde et al. | |
| 2012/0123581 A1* | 5/2012 | Smilde | G03F 7/70483 700/105 |
| 2012/0162755 A1 | 6/2012 | Stroessner et al. | |
| 2012/0206729 A1 | 8/2012 | Seligson et al. | |
| 2012/0224183 A1 | 9/2012 | Fay et al. | |
| 2012/0243004 A1 | 9/2012 | El Gawhary et al. | |
| 2012/0249989 A1 | 10/2012 | Fujii | |
| 2012/0327503 A1 | 12/2012 | Manassen et al. | |
| 2013/0114085 A1 | 5/2013 | Wang et al. | |
| 2013/0141730 A1 | 6/2013 | Quintanilha | |
| 2013/0258310 A1 | 10/2013 | Smilde et al. | |
| 2013/0271740 A1 | 10/2013 | Quintanilha | |
| 2016/0091422 A1* | 3/2016 | Van Der Zouw | G01N 21/4738 356/445 |

OTHER PUBLICATIONS

Written Opinion of the International Searching Authority directed to related Patent Application No. PCT/EP2015/065984, mailed Sep. 11, 2015; 8 pages.

"Apodization," Wikipedia, the Free Encyclopedia, accessed at https://en.wikipedia.org/wiki/Apodization on Oct. 29, 2015; 2 pages.

"Liquid crystal," Wikipedia, the Free Encyclopedia, accessed at https://en.wikipedia.org/wiki/Liquid_crystal on Oct. 29, 2015; 15 pages.

"Liquid crystal on silicon," Wikipedia, the Free Encyclopedia, accessed at https://en.wikipedia.org/wiki/Liquid_crystal_on_silicon on Oct. 29, 2015; 5 pages.

"Polarizer," Wikipedia, the Free Encyclopedia, accessed at https://en.wikipedia.org/wiki/Polarizer on Oct. 29, 2015; 12 pages.

"Spatial light modulator," Wikipedia, the Free Encyclopedia, accessed at https://en.wikipedia.org/wiki/Spatial_light_modulator on Oct. 29, 2015; 3 pages.

* cited by examiner

ILLUMINATION SYSTEM, INSPECTION APPARATUS INCLUDING SUCH AN ILLUMINATION SYSTEM, INSPECTION METHOD AND MANUFACTURING METHOD

CROSS REFERENCE TO RELATED APPLICATIONS

This application claims benefit of EP Patent Application No 14178791.1, filed on Jul. 28, 2014.

This application claims benefit of EP Patent Application No 14191958.9, filed on Nov. 5, 2014.

BACKGROUND

Field of the Invention

The present invention relates to inspection apparatus and methods usable, for example, to perform metrology in the manufacture of devices by lithographic techniques. The invention further relates to an illumination system for use in such inspection apparatus and to methods of manufacturing devices using lithographic techniques.

Background Art

A lithographic apparatus is a machine that applies a desired pattern onto a substrate, usually onto a target portion of the substrate. A lithographic apparatus can be used, for example, in the manufacture of integrated circuits (ICs). In that instance, a patterning device, which is alternatively referred to as a mask or a reticle, may be used to generate a circuit pattern to be formed on an individual layer of the IC. This pattern can be transferred onto a target portion (e.g., including part of, one, or several dies) on a substrate (e.g., a silicon wafer). Transfer of the pattern is typically via imaging onto a layer of radiation-sensitive material (resist) provided on the substrate. In general, a single substrate will contain a network of adjacent target portions that are successively patterned.

In lithographic processes, it is desirable frequently to make measurements of the structures created, e.g., for process control and verification. Various tools for making such measurements are known, including scanning electron microscopes, which are often used to measure critical dimension (CD), and specialized tools to measure overlay, the accuracy of alignment of two layers in a device. Recently, various forms of scatterometers have been developed for use in the lithographic field. These devices direct a beam of radiation onto a target and measure one or more properties of the scattered radiation—e.g., intensity at a single angle of reflection as a function of wavelength; intensity at one or more wavelengths as a function of reflected angle; or polarization as a function of reflected angle—to obtain a diffraction "spectrum" from which a property of interest of the target can be determined.

Examples of known scatterometers include angle-resolved scatterometers of the type described in US2006033921A1 and US2010201963A1. The targets used by such scatterometers are relatively large, e.g., 40 µm by 40 µm, gratings and the measurement beam generates a spot that is smaller than the grating (i.e., the grating is underfilled). In addition to measurement of feature shapes by reconstruction, diffraction based overlay can be measured using such apparatus, as described in published patent application US2006066855A1. Diffraction-based overlay metrology using dark-field imaging of the diffraction orders enables overlay measurements on smaller targets. Examples of dark field imaging metrology can be found in international patent applications US20100328655A1 and US2011069292A1 which documents are hereby incorporated by reference in their entirety. Further developments of the technique have been described in published patent publications US20110027704A, US20110043791A, US2011102753A1, US20120044470A, US20120123581A, US20130258310A, US20130271740A and WO2013178422A1. These targets can be smaller than the illumination spot and may be surrounded by product structures on a wafer. Multiple gratings can be measured in one image, using a composite grating target. The contents of all these applications are also incorporated herein by reference.

As is known, each product and process requires care in the design of metrology targets and the selection of an appropriate metrology 'recipe' by which overlay measurements will be performed. In the known metrology technique, diffraction patterns and/or dark field images of a metrology target are captured while the target is illuminated under desired illumination conditions. These illumination conditions are defined in the metrology recipe by various illumination parameters such as the wavelength of the radiation, its angular intensity distribution (illumination profile) and its polarization. The inspection apparatus includes an illumination system comprising one or more radiation sources and an illumination system for the delivery of the illumination with the desired illumination parameters. In practice, it will be desired that the illumination system can switch between different modes of illumination by changing these parameters between measurements. In the following, the term 'light' will be used for convenience to refer the illuminating radiation, without implying any limitation to visible wavelengths.

In one commercially available apparatus, the illumination system includes firstly a pair of shutters and polarizing beam splitter device, to select between two possible polarization of radiation. This is followed by an aperture selection device, defining the desired angular distribution of the light. There are several moving parts in the known illumination system, making it sensitive to vibrations and wear. These moving parts are in both the selection of polarization and the aperture selection device. Another published patent application US20130141730A1 proposes to generate illumination profiles with customized color and/or polarization distribution. The customized profiles in that case are achieved by switching between different fibers of a fiber bundle. A fiber switching system is provided to couple a fiber with desired color and polarization o light to a fiber delivering light to a specific location in an illumination pupil.

As an alternative to moving aperture selection devices, some of the above publications mentioned that a programmable spatial light modulator (SLM) such as a deformable mirror array or liquid crystal (LC) transmissive SLM can be used also. In principle, such devices should enable a more compact design with fewer moving parts. However, in practice these devices have not been implemented for the illuminator. One reason for this may be that providing reflective programmable SLMs such as DMDs in the illumination path requires convoluted beam paths and cause layout difficulties. A problem with LC shutter type devices is that they generally deliver only one polarization of light, while metrology applications require freedom to control polarization as an illumination parameter in the recipe.

US20070279630 (KLA) discloses an 'order selected' microscope for overlay metrology in semiconductor manufacturing. It is said that a spatial light modulator (SLM) device can be provided in one or both of an illumination path and an imaging path. Examples of SLM include chrome-on-glass patterns, and may provide an apodization function, rather than selection. For the imaging path, it is mentioned that a liquid crystal transmissive or reflective pixilated element or a DMD (digital micro-mirror device) may be used. However, this is not mentioned for the illumination path, and polarization as an illumination parameter is not discussed at all.

SUMMARY OF THE INVENTION

The present invention aims to provide alternative illumination systems for metrology and other applications in which an illumination profile can be selected by a programmable device, without some of the compromises that would otherwise result. For example, the invention may maintain greater freedom to control other illumination parameters such as polarization or wavelength. For example, the invention in some embodiments aims to enable the use of liquid crystal transmissive SLM without unduly restricting polarization as an illumination parameter.

The invention in a first aspect provides an illumination system for conditioning a beam of radiation in an illumination path of an optical system, the illumination system comprising:

a beam combiner having a first input path, a second input path and an output path, a first spatial light modulator for receiving first radiation and spatially modulating the first radiation in accordance with a first programmable pattern;

a second spatial light modulator for receiving second radiation and spatially modulating the second radiation in accordance with a second programmable pattern; and one or more polarizing elements, wherein the beam combiner is configured to receive the spatially modulated first radiation via said first input path, to receive the spatially modulated second radiation via said second input path and to output spatially modulated combined radiation via said output path;

and wherein the polarizing elements, the spatial light modulators and the beam combiner are configured such that the combined radiation has a first polarized component in portions of the output path determined by the first programmable pattern and has a second polarized component in portions of the output path determined by the second programmable pattern.

The illumination system can be implemented in a variety of ways and using a variety of components.

In one example embodiment, the first spatial light modulator is configured to vary a polarization state of the first radiation in portions of the first input path determined by the first programmable pattern, while the second spatial light modulator is configured to vary a polarization state of the second radiation in portions of the second input path determined by the second programmable pattern. The polarizing elements include pre-polarizers for applying polarization to the first and second radiation prior to the spatial light modulators. The beam combiner comprises a polarizing beam splitter. The polarizing beam splitter selectively transmits the spatially modulated first radiation from the first input path of the beam combiner to the output path, depending on the polarization state of the spatially modulated first radiation. The polarizing beam splitter selectively transmits the spatially modulated second radiation from the second input path of the beam combiner to the output path, depending on the polarization state of the spatially modulated second radiation.

In a particular example, the first and second spatial light modulators lie in a common plane and are formed by different portions of a single liquid crystal cell.

In a case where an optical path length to the output path from the first spatial light modulator to the output path would be different to the optical path length from the second spatial light modulator to the output path, a path length compensator may be provided between one of the spatial light modulators and the beam combiner.

In a second example, the beam combiner comprises a polarizing beam splitter, the polarizing beam splitter selectively transmitting the spatially modulated first radiation from the first input path of the beam combiner to the output path, depending on the polarization state of the spatially modulated first radiation. The polarizing elements include a first pre-polarizer for applying polarization to the first radiation prior to the first spatial light modulator. The polarizing beam splitter is arranged to serve simultaneously as the first pre-polarizer and the beam combiner.

The polarizing beam splitter in such an example may be further configured to selectively deliver the second radiation from the second input path of the beam combiner to the output path, depending on the polarization state of the spatially modulated second radiation. The polarizing elements may include a second pre-polarizer for applying polarization to the second radiation prior to the second spatial light modulator. The polarizing beam splitter may then be arranged to serve simultaneously as the first pre-polarizer, the second pre-polarizer and the beam combiner.

In a particular example, the polarizing beam splitter includes a partially reflecting surface. The partially reflecting surface is configured to pre-polarize the first radiation by transmission through the partially reflecting surface and to deliver the spatially modulated first radiation to the output path by reflection from the partially reflecting surface, and simultaneously to pre-polarize the second radiation by reflection from the partially reflecting surface and to deliver the spatially modulated second radiation to the output path by transmission through the partially reflecting surface.

The invention in a second aspect provides an illumination system for conditioning a beam of radiation, for example in an inspection apparatus, the illumination system comprising at least a first spatial light modulator for imparting a programmable first illumination profile to first radiation in a first optical path and a second spatial light modulator for imparting a programmable second illumination profile to second radiation in a second optical path, the illumination system further being arranged to combine the first radiation and second radiation so as to superimpose the first and second illumination profiles in an illumination path of the inspection apparatus, wherein the first radiation delivered to the illumination path from the first spatial light modulator has a first characteristic and the second radiation delivered to the illumination path from the second spatial light modulator has a second characteristic, in addition to any differences in illumination profile.

The invention yet further provides an inspection apparatus comprising:

a support for a substrate an illumination system for illuminating one or more structures of interest formed the substrate with radiation having desired characteristics, and a detection system for detecting radiation scattered by the substrate to obtain a measurement of a property of one or more structures of interest on the substrate, wherein the illumination system comprises an illumination system according to any aspect of the invention as set forth defined above, and wherein the inspection apparatus further comprises a controller for controlling the first and second spatial light modulators to implement a measurement-specific first programmable pattern and second programmable pattern for each measurement in a series of different measurements.

The first and second spatial light modulators may be located effectively in a pupil plane of the illumination system. In this way the amount and polarization state of radiation incident on a target from different angles of incidence may be controlled.

Alternatively or in addition, first and second spatial light modulators may be located effectively in a field plane of the illumination system. In this way, the amount and polarization state of radiation incident on different parts of a target may be controlled.

The invention in the first aspect yet further provides a method of manufacturing devices wherein a device pattern is applied to a series of substrates using a lithographic process, the method including:

using an inspection apparatus according to any aspect of the invention as set forth above to measure a property of at least one structure of interest formed on at least one of said substrates, and controlling the lithographic process for later substrates in accordance with the measured property.

The invention in yet further provides a computer program product comprising machine-readable instructions for causing a processor to control the first and second spatial light modulators in an inspection apparatus according to the invention as set forth above, thereby to implement a plurality of illumination modes, each illumination mode defining a specific combination of first and second programmable patterns.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF EXEMPLARY EMBODIMENTS

Before describing embodiments of the invention in detail, it is instructive to present an example environment in which embodiments of the present invention may be implemented.

Figure 1:
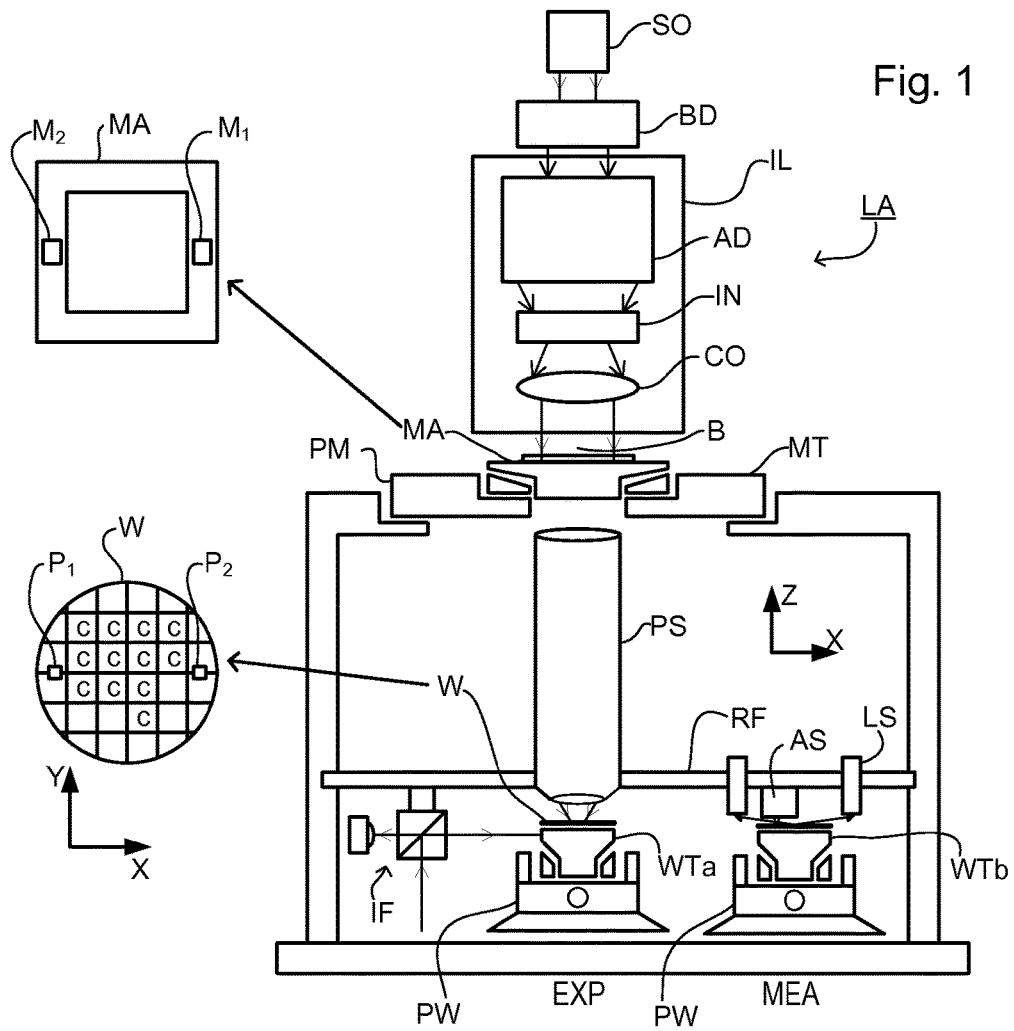
FIG. 1 depicts a lithographic apparatus.

FIG. 1 schematically depicts a lithographic apparatus LA. The apparatus includes an illumination system (illuminator) IL configured to condition a radiation beam B (e.g., UV radiation or DUV radiation), a patterning device support or support structure (e.g., a mask table) MT constructed to support a patterning device (e.g., a mask) MA and connected to a first positioner PM configured to accurately position the patterning device in accordance with certain parameters; two substrate tables (e.g., a wafer table) WTa and WTb each constructed to hold a substrate (e.g., a resist coated wafer) W and each connected to a second positioner PW configured to accurately position the substrate in accordance with certain parameters; and a projection system (e.g., a refractive projection lens system) PS configured to project a pattern imparted to the radiation beam B by patterning device MA onto a target portion C (e.g., including one or more dies) of the substrate W. A reference frame RF connects the various components, and serves as a reference for setting and measuring positions of the patterning device and substrate and of features on them.

The illumination system may include various types of optical components, such as refractive, reflective, magnetic, electromagnetic, electrostatic or other types of optical components, or any combination thereof, for directing, shaping, or controlling radiation.

The patterning device support holds the patterning device in a manner that depends on the orientation of the patterning device, the design of the lithographic apparatus, and other conditions, such as for example whether or not the patterning device is held in a vacuum environment. The patterning device support can take many forms. The patterning device support may ensure that the patterning device is at a desired position, for example with respect to the projection system.

The term "patterning device" used herein should be broadly interpreted as referring to any device that can be used to impart a radiation beam with a pattern in its cross-section such as to create a pattern in a target portion of the substrate. It should be noted that the pattern imparted to the radiation beam may not exactly correspond to the desired pattern in the target portion of the substrate, for example if the pattern includes phase-shifting features or so called assist features. Generally, the pattern imparted to the radiation beam will correspond to a particular functional layer in a device being created in the target portion, such as an integrated circuit.

As here depicted, the apparatus is of a transmissive type (e.g., employing a transmissive patterning device). Alternatively, the apparatus may be of a reflective type (e.g., employing a programmable mirror array of a type as referred to above, or employing a reflective mask). Examples of patterning devices include masks, programmable mirror arrays, and programmable liquid crystal display (LCD) panels. Any use of the terms "reticle" or "mask" herein may be considered synonymous with the more general term "patterning device." The term "patterning device" can also be interpreted as referring to a device storing in digital form pattern information for use in controlling such a programmable patterning device.

The term "projection system" used herein should be broadly interpreted as encompassing any type of projection system, including refractive, reflective, catadioptric, magnetic, electromagnetic and electrostatic optical systems, or any combination thereof, as appropriate for the exposure radiation being used, or for other factors such as the use of an immersion liquid or the use of a vacuum. Any use of the term "projection lens" herein may be considered as synonymous with the more general term "projection system".

The lithographic apparatus may also be of a type wherein at least a portion of the substrate may be covered by a liquid having a relatively high refractive index, e.g., water, so as to fill a space between the projection system and the substrate. An immersion liquid may also be applied to other spaces in the lithographic apparatus, for example, between the mask and the projection system. Immersion techniques are well known in the art for increasing the numerical aperture of projection systems.

In operation, the illuminator IL receives a radiation beam from a radiation source SO. The source and the lithographic apparatus may be separate entities, for example when the source is an excimer laser. In such cases, the source is not considered to form part of the lithographic apparatus and the radiation beam is passed from the source SO to the illuminator IL with the aid of a beam delivery system BD including, for example, suitable directing mirrors and/or a beam expander. In other cases the source may be an integral part of the lithographic apparatus, for example when the source is a mercury lamp. The source SO and the illuminator IL, together with the beam delivery system BD if required, may be referred to as a radiation system.

The illuminator IL may for example include an adjuster AD for adjusting the angular intensity distribution of the radiation beam, an integrator IN and a condenser CO. The illuminator may be used to condition the radiation beam, to have a desired uniformity and intensity distribution in its cross section.

The radiation beam B is incident on the patterning device MA, which is held on the patterning device support MT, and is patterned by the patterning device. Having traversed the patterning device (e.g., mask) MA, the radiation beam B passes through the projection system PS, which focuses the beam onto a target portion C of the substrate W. With the aid of the second positioner PW and position sensor IF (e.g., an interferometric device, linear encoder, 2-D encoder or capacitive sensor), the substrate table WTa or WTb can be moved accurately, e.g., so as to position different target portions C in the path of the radiation beam B. Similarly, the first positioner PM and another position sensor (which is not explicitly depicted in FIG. 1) can be used to accurately position the patterning device (e.g., mask) MA with respect to the path of the radiation beam B, e.g., after mechanical retrieval from a mask library, or during a scan.

Patterning device (e.g., mask) MA and substrate W may be aligned using mask alignment marks M1, M2 and substrate alignment marks P1, P2. Although the substrate alignment marks as illustrated occupy dedicated target portions, they may be located in spaces between target portions (these are known as scribe-lane alignment marks). Similarly, in situations in which more than one die is provided on the patterning device (e.g., mask) MA, the mask alignment marks may be located between the dies. Small alignment mark may also be included within dies, in amongst the device features, in which case it is desirable that the markers be as small as possible and not require any different imaging or process conditions than adjacent features. The alignment system, which detects the alignment markers is described further below.

The depicted apparatus could be used in a variety of modes. In a scan mode, the patterning device support (e.g., mask table) MT and the substrate table WT are scanned synchronously while a pattern imparted to the radiation beam is projected onto a target portion C (i.e., a single dynamic exposure). The speed and direction of the substrate table WT relative to the patterning device support (e.g., mask table) MT may be determined by the (de-)magnification and image reversal characteristics of the projection system PS. In scan mode, the maximum size of the exposure field limits the width (in the non-scanning direction) of the target portion in a single dynamic exposure, whereas the length of the scanning motion determines the height (in the scanning direction) of the target portion. Other types of lithographic apparatus and modes of operation are possible, as is well-known in the art. For example, a step mode is known. In so-called "maskless" lithography, a programmable patterning device is held stationary but with a changing pattern, and the substrate table WT is moved or scanned.

Combinations and/or variations on the above described modes of use or entirely different modes of use may also be employed.

Lithographic apparatus LA is of a so-called dual stage type which has two substrate tables WTa, WTb and two stations—an exposure station EXP and a measurement station MEA—between which the substrate tables can be exchanged. While one substrate on one substrate table is being exposed at the exposure station, another substrate can be loaded onto the other substrate table at the measurement station and various preparatory steps carried out. This enables a substantial increase in the throughput of the apparatus. The preparatory steps may include mapping the surface height contours of the substrate using a level sensor LS and measuring the position of alignment markers on the substrate using an alignment sensor AS. If the position sensor IF is not capable of measuring the position of the substrate table while it is at the measurement station as well as at the exposure station, a second position sensor may be provided to enable the positions of the substrate table to be tracked at both stations, relative to reference frame RF. Other arrangements are known and usable instead of the dual-stage arrangement shown. For example, other lithographic apparatuses are known in which a substrate table and a measurement table are provided. These are docked together when performing preparatory measurements, and then undocked while the substrate table undergoes exposure.

Figure 2:
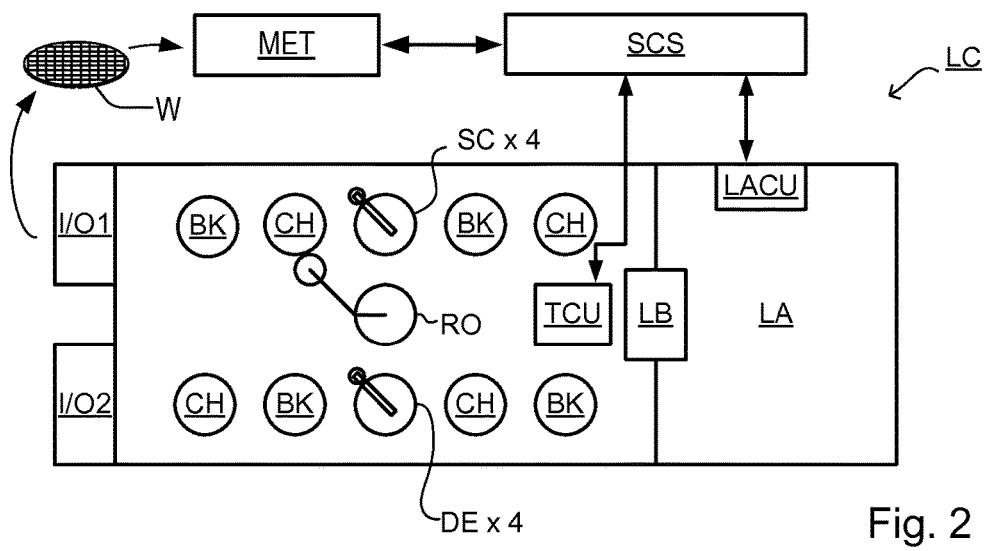
FIG. 2 depicts a lithographic cell or cluster in which an inspection apparatus according to the present invention may be used.

As shown in FIG. 2, the lithographic apparatus LA forms part of a lithographic cell LC, also sometimes referred to a lithocell or cluster, which also includes apparatus to perform pre- and post-exposure processes on a substrate. Conventionally these include spin coaters SC to deposit resist layers, developers DE to develop exposed resist, chill plates CH and bake plates BK. A substrate handler, or robot, RO picks up substrates from input/output ports I/O1, I/O2, moves them between the different process apparatus and delivers then to the loading bay LB of the lithographic apparatus. These devices, which are often collectively referred to as the track, are under the control of a track control unit TCU which is itself controlled by the supervisory control system SCS, which also controls the lithographic apparatus via lithography control unit LACU. Thus, the different apparatus can be operated to maximize throughput and processing efficiency.

In order that the substrates that are exposed by the lithographic apparatus are exposed correctly and consistently, it is desirable to inspect exposed substrates to measure properties such as overlay errors between subsequent layers, line thicknesses, critical dimensions (CD), etc. Accordingly a manufacturing facility in which lithocell LC is located also includes metrology system MET which receives some or all of the substrates W that have been processed in the lithocell. Metrology results are provided directly or indirectly to the supervisory control system SCS. If errors are detected, adjustments may be made to exposures of subsequent substrates, especially if the inspection can be done soon and fast enough that other substrates of the same batch are still to be exposed. Also, already exposed substrates may be stripped and reworked to improve yield, or discarded, thereby avoiding performing further processing on substrates that are known to be faulty. In a case where only some target portions of a substrate are faulty, further exposures can be performed only on those target portions which are good.

Within metrology system MET, an inspection apparatus is used to determine the properties of the substrates, and in particular, how the properties of different substrates or different layers of the same substrate vary from layer to layer. The inspection apparatus may be integrated into the lithographic apparatus LA or the lithocell LC or may be a stand-alone device. To enable most rapid measurements, it is desirable that the inspection apparatus measure properties in the exposed resist layer immediately after the exposure. However, the latent image in the resist has a very low contrast—there is only a very small difference in refractive index between the parts of the resist which have been exposed to radiation and those which have not—and not all inspection apparatus have sufficient sensitivity to make useful measurements of the latent image. Therefore measurements may be taken after the post-exposure bake step (PEB) which is customarily the first step carried out on exposed substrates and increases the contrast between exposed and unexposed parts of the resist. At this stage, the image in the resist may be referred to as semi-latent. It is also possible to make measurements of the developed resist image—at which point either the exposed or unexposed parts of the resist have been removed—or after a pattern transfer step such as etching. The latter possibility limits the possibilities for rework of faulty substrates but may still provide useful information.

Figure 3:
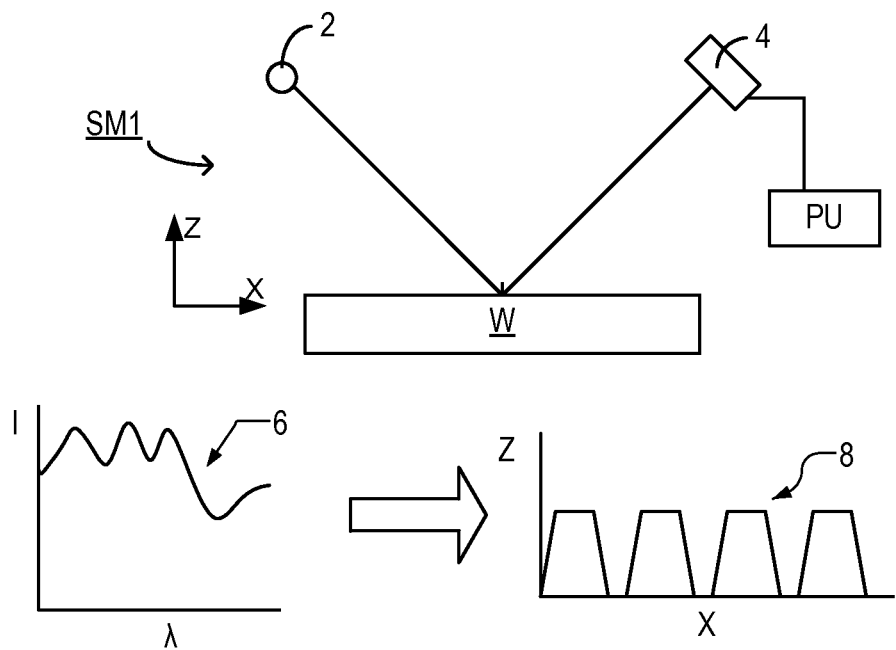
FIG. 3 illustrates the principles of operation of a spectroscopic scatterometer as a first example of an inspection apparatus.

FIG. 3 depicts a known spectroscopic scatterometer which may be used as an inspection apparatus in a metrology system of the type described above. It comprises a broadband (white light) radiation projector 2 which projects radiation onto a substrate W. The reflected radiation is passed to a spectrometer 4, which measures a spectrum 6 (intensity as a function of wavelength) of the specular reflected radiation. From this data, the structure or profile 8 giving rise to the detected spectrum may be reconstructed by calculation within processing unit PU. The reconstruction can be performed for example by Rigorous Coupled Wave Analysis and non-linear regression, or comparison with a library of pre-measured spectra or pre-computed simulated spectra. In general, for the reconstruction the general form of the structure is known and some parameters are assumed from knowledge of the process by which the structure was made, leaving only a few parameters of the structure to be determined from the scatterometry data. Such a scatterometer may be configured as a normal-incidence scatterometer or an oblique-incidence scatterometer.

Figure 4:
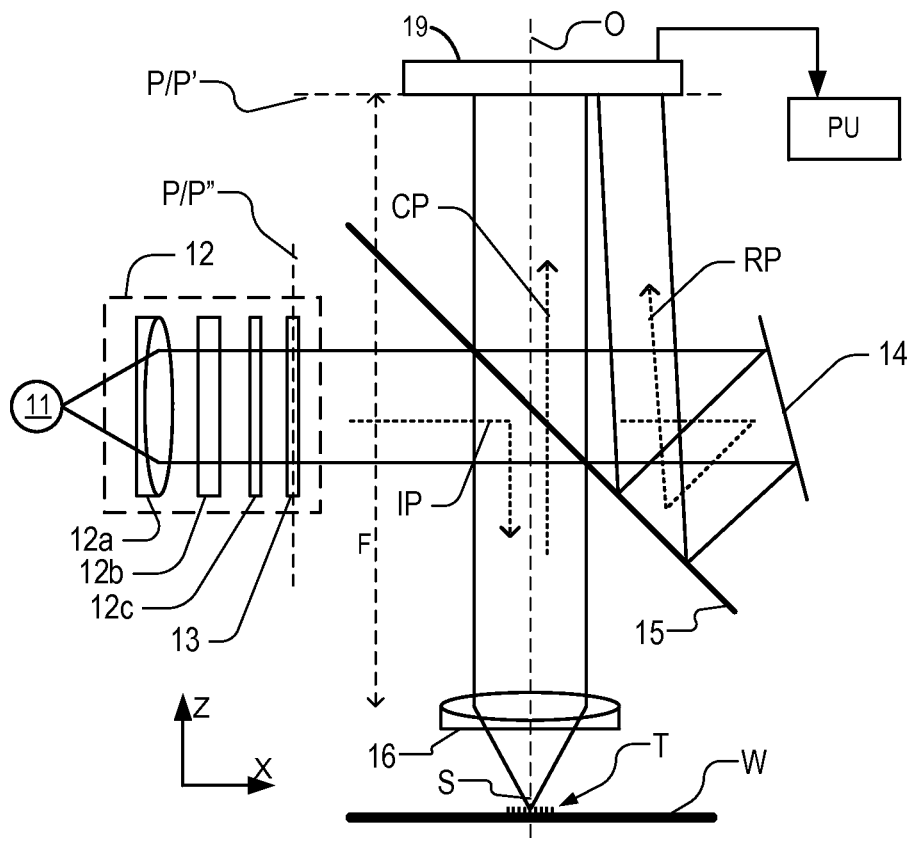
FIG. 4 illustrates in schematic form an angle-resolved scatterometer as another example of an inspection apparatus.

FIG. 4 shows the basic elements of a known angle-resolved scatterometer that may be used instead of or in addition to a spectroscopic scatterometer. In this type of inspection apparatus, radiation emitted by a radiation source 11 is conditioned by an illumination system 12. For example, illumination system 12 may include a collimating using lens system 12a, a color filter 12b, a polarizer 12c and an aperture device 13. The conditioned radiation follows an illumination path IP, in which it is reflected by partially reflecting surface 15 and focused into a spot S on substrate W via a microscope objective lens 16. A metrology target T may be formed on substrate W. Lens 16, has a high numerical aperture (NA), preferably at least 0.9 and more preferably at least 0.95. Immersion fluid can be used to obtain with numerical apertures over 1 if desired.

As in the lithographic apparatus LA, one or more substrate tables may be provided to hold the substrate W during measurement operations. The substrate tables may be similar or identical in form to the substrate tables WTa, WTb of FIG. 1. (In an example where the inspection apparatus is integrated with the lithographic apparatus, they may even be the same substrate tables.) Coarse and fine positioners may be configured to accurately position the substrate in relation to a measurement optical system. Various sensors and actuators are provided for example to acquire the position of a target of interest, and to bring it into position under the objective lens 16. Typically many measurements will be made on targets at different locations across substrate W. The substrate support can be moved in X and Y directions to acquire different targets, and in the Z direction to obtain a desired focusing of the optical system on the target. It is convenient to think and describe operations as if the objective lens and optical system being brought to different locations on the substrate, when in practice the optical system remains substantially stationary and only the substrate moves. Provided the relative position of the substrate and the optical system is correct, it does not matter in principle whether one or both of those is moving in the real world.

When the radiation beam is incident on the beam splitter 16 part of it is transmitted through the beam splitter and follows a reference path RP towards a reference mirror 14.

Radiation reflected by the substrate, including radiation diffracted by any metrology target T, is collected by lens 16 and follows a collection path CP in which it passes through partially reflecting surface 15 into a detector 19. The detector may be located in the back-projected pupil plane P, which is at the focal length F of the lens 16. In practice, the pupil plane itself may be inaccessible, and may instead be reimaged with auxiliary optics (not shown) onto the detector located in a so-called conjugate pupil plane P'. The detector is preferably a two-dimensional detector so that a two-dimensional angular scatter spectrum or diffraction spectrum of a metrology target T can be measured. In the pupil plane or conjugate pupil plane, the radial position of radiation defines the angle of incidence/departure of the radiation in the plane of focused spot S, and the angular position around an optical axis O defines azimuth angle of the radiation. The detector 19 may be, for example, an array of CCD or CMOS sensors, and may use an integration time of, for example, 40 milliseconds per frame.

Radiation in reference path RP is projected onto a different part of the same detector 19 or alternatively on to a different detector (not shown). A reference beam is often used for example to measure the intensity of the incident radiation, to allow normalization of the intensity values measured in the scatter spectrum.

The various components of illumination system 12 can be adjustable to implement different metrology 'recipes' within the same apparatus. Color filter 12b may be implemented for example by a set of interference filters to select different wavelengths of interest in the range of, say, 405-790 nm or even lower, such as 200-300 nm. An interference filter may be tunable rather than comprising a set of different filters. A grating could be used instead of interference filters. Polarizer 12c may be rotatable or swappable so as to implement different polarization states in the radiation spot S. Aperture device 13 can be adjusted to implement different illumination profiles. Aperture device 13 is located in a plane P'" conjugate with pupil plane P of objective lens 16 and the plane of the detector 19. In this way, an illumination profile defined by the aperture device defines the angular distribution of light incident on substrate radiation passing through different locations on aperture device 13.

The detector 19 may measure the intensity of scattered light at a single wavelength (or narrow wavelength range), the intensity separately at multiple wavelengths or integrated over a wavelength range. Furthermore, the detector may separately measure the intensity of transverse magnetic- and transverse electric-polarized light and/or the phase difference between the transverse magnetic- and transverse electric-polarized light.

Where a metrology target T is provided on substrate W, this may be a 1-D grating, which is printed such that after development, the bars are formed of solid resist lines. The target may be a 2-D grating, which is printed such that after development, the grating is formed of solid resist pillars or vias in the resist. The bars, pillars or vias may alternatively be etched into the substrate. This pattern is sensitive to chromatic aberrations in the lithographic projection apparatus, particularly the projection system PS. Illumination symmetry and the presence of such aberrations will manifest themselves in a variation in the printed grating. Accordingly, the scatterometry data of the printed gratings is used to reconstruct the gratings. The parameters of the 1-D grating, such as line widths and shapes, or parameters of the 2-D grating, such as pillar or via widths or lengths or shapes, may be input to the reconstruction process, performed by processing unit PU, from knowledge of the printing step and/or other scatterometry processes.

In addition to measurement of parameters by reconstruction, angle resolved scatterometry is useful in the measurement of asymmetry of features in product and/or resist patterns. A particular application of asymmetry measurement is for the measurement of overlay, where the target comprises one set of periodic features superimposed on another. The concepts of asymmetry measurement using the instrument of FIG. 3 or 4 are described for example in published patent application US2006066855A1 cited above. Simply stated, while the positions of the diffraction orders in the diffraction spectrum of the target are determined only by the periodicity of the target, asymmetry of intensity levels in the diffraction spectrum is indicative of asymmetry in the individual features which make up the target. In the instrument of FIG. 4, where detector 19 may be an image sensor, such asymmetry in the diffraction orders appears directly as asymmetry in the pupil image recorded by detector 19. This asymmetry can be measured by digital image processing in unit PU, and calibrated against known values of overlay.

Figure 5A:
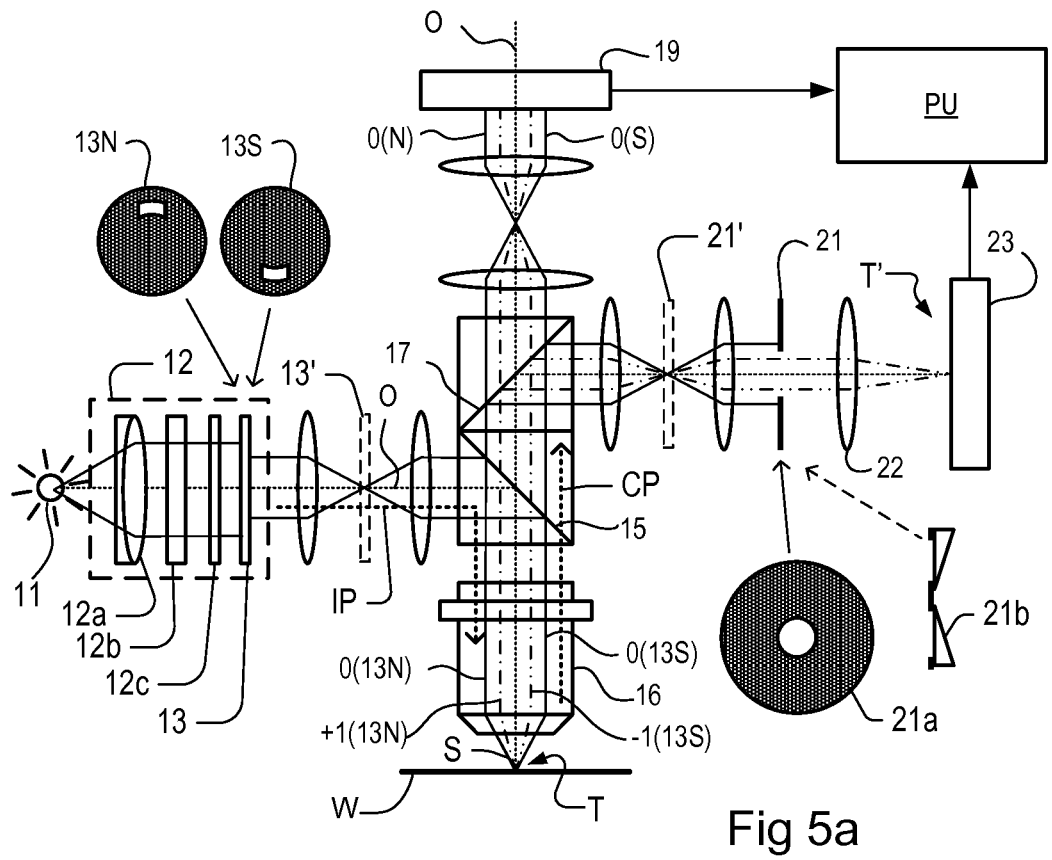
FIGS. 5a and 5b illustrate schematically an inspection apparatus adapted to perform angle-resolved scatterometry and dark-field imaging inspection methods.

FIG. 5a shows in more detail an inspection apparatus implementing angle-resolved scatterometry by the same principles as the apparatus of FIG. 4, with additional adaptations for performing so-called dark field imaging. The apparatus may be a stand-alone device or incorporated in either the lithographic apparatus LA, e.g., at the measurement station, or the lithographic cell LC. An optical axis, which has several branches throughout the apparatus, is represented by a dotted line O. A target grating T and diffracted rays are illustrated in more detail in FIG. 5b.

The same reference numbers are used for components described already in the FIG. 4 apparatus. The illumination path is labeled IP as before. The reference path RP is omitted, for clarity. Compared with that apparatus, a second beam splitter 17 divides the collection path into two branches. In a first measurement branch, detector 19 records a scatter spectrum or diffraction spectrum of the target exactly as described above. This detector 19 may be referred to as the pupil image detector.

In the second measurement branch, imaging optical system 22 forms an image of the target on the substrate W on sensor 23 (e.g. a CCD or CMOS sensor). An aperture stop 21 is provided in a plane that is in the collection path in a plane conjugate to the pupil-plane (it may also be called a pupil stop). Aperture stop 21 can take different forms, just as the illumination aperture can take different forms. Examples 21a and 21b will be discussed below. Typically, aperture stop 21 functions to block the zeroth order diffracted beam so that the image of the target formed on sensor 23 is formed only from the first order beam(s). This is the so-called dark field image, equivalent to dark field microscopy. The images captured by sensors 19 and 23 are output to image processor and controller PU, the function of which will depend on the particular type of measurements being performed.

In the illumination path in this example, additional optics are shown such that a field stop 13' can be placed in a plane conjugate with the plane of the target and the image sensor 23. This plane may be referred to as a field plane, or conjugate image plane, and has the property that each spatial position across the field plane corresponds to a position across the target. This field stop may be used for example to shape the illumination spot for a particular purpose, or simply to avoid illuminating features that are within the field of view of the apparatus but not part of the target of interest. The following drawings and discussion refer, by way of example, to techniques for implementation of the function of aperture device 13, but the present disclosure also encompasses use of the same techniques to implement the function of field stop 13'.

Figure 6:
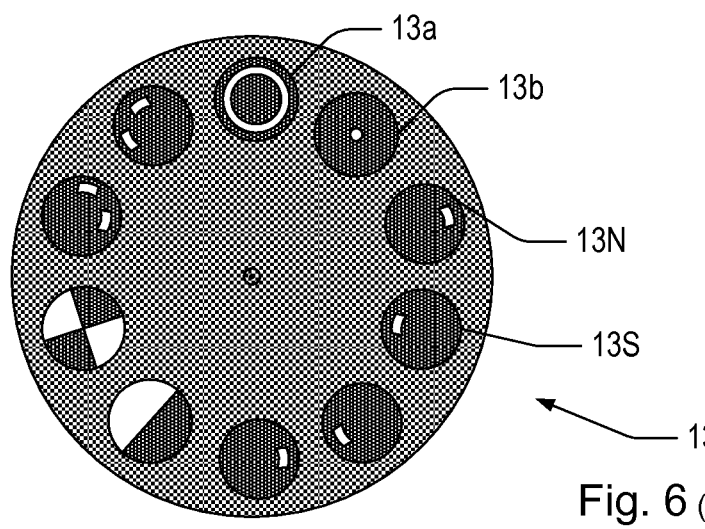
FIG. 6 illustrates schematically an aperture device used in the illumination system of a known inspection apparatus.

FIG. 6 shows an example aperture device 13. This takes the form of a wheel, in which a variety of apertures 13a, 13b, 13N, 13S can be selected and positions in the beam path of illumination system 12. As already mentioned, the angular range at which the radiation is incident on the substrate can be selected by defining a spatial intensity distribution in a plane that presents the spatial spectrum of the substrate plane, here referred to as a (conjugate) pupil plane. In particular, this can be done conventionally by selecting an aperture of suitable form in the path of collimated radiation coming from lens 12a.

Using, for example, aperture 13a, we obtain an annular illumination profile, centered on the optical axis of the illumination system. The radiation in measurement spot S will be incident on substrate W in a cone of angles not encompassing the normal to the substrate. In other words, the aperture 13a can be used to provide an off-axis illumination profile.

Figure 5B:
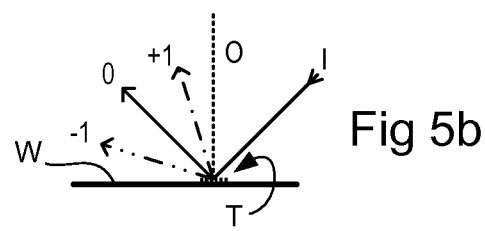

As shown in more detail in FIG. 5b, target grating T is placed with substrate W normal to the optical axis O of objective lens 16. In the case of an off-axis illumination profile, A ray of illumination I impinging on grating T from an angle off the axis O gives rise to a zeroth order ray (solid line 0) and two first order rays (dot-chain line +1 and double dot-chain line −1). It should be remembered that with an overfilled small target grating, these rays are just one of many parallel rays covering the area of the substrate including metrology target grating T and other features. Since the annular aperture 13a in plate 13 has a finite width (necessary to admit a useful quantity of light, the incident rays I will in fact occupy a range of angles, and the diffracted rays 0 and +1/−1 will be spread out somewhat. According to the point spread function of a small target, each order +1 and −1 will be further spread over a range of angles, not a single ideal ray as shown.

Other modes of illumination are possible by using different apertures. For example, aperture 13b provides on-axis illumination. Apertures 13N ('north') and 13S ('south') each provide off-axis illumination from a specific narrow range of angles only. Returning to FIG. 5a, this is illustrated by designating diametrically opposite portions of the annular aperture as north (N) and south (S). The +1 diffracted rays from the north portion of the cone of illumination, which are labeled +1(13N), enter the objective lens 16, and so do the −1 diffracted rays from the south portion of the cone (labeled −1(13S)). As described in the prior applications mentioned in the introduction, using the dark-field imaging sensor 23 while switching between apertures 13N, 13S of this type is one way of obtaining asymmetry measurements from multiple small targets. Aperture stop 21a can be used to block the zeroth order radiation when using off-axis illumination.

While off-axis illumination is shown, on-axis illumination of the targets may instead be used and an aperture stop 13b with an off-axis aperture is used to pass substantially only one first order of diffracted light to the sensor. In one example, prisms 21b are used in place of aperture stop 21 which have the effect of diverting the +1 and −1 orders to different locations on sensor 23 so that they can be detected and compared without making two images. This technique, is disclosed in the above-mentioned published patent application US2011102753A1, the contents of which are hereby incorporated by reference. 2nd, 3rd and higher order beams (not shown in FIG. 5) can be used in measurements, instead of or in addition to the first order beams.

Illumination profiles can be varied greatly and the use of custom illumination is becoming more and more important in both lithography and optical metrology. The customization of the illumination enables improvement of the measurement quality (TMU, cross-correlation and sensitivity). Just a few examples of illumination profiles are shown in FIG. 6.

FIG. 7 shows schematic detail of illumination system 12 as implemented in one commercial apparatus. Components of the illumination system corresponding to those shown in FIGS. 4 and 5 are represented by the same reference signs, but with prefix '1'. The illumination system is shown in two different operating states a and b. The illumination system has separately operable branches, according to which polarization is required. Components in these branches are labelled with suffix 'S' or 'P'. Radiation source 111 feeds these two branches through fibers 130-S and 130-P. (Alternatively, each branch could have its own radiation source 111-S, 111-P.) Shutter devices 132-S and 132-P are provided to admit or block radiation into the respective path, according to a control signal. The shutter devices may be piezo-electric shutters, for example. Each branch has a collimating lens system 112a-S, 112a-P. Wavelength filter 12b is not shown. The skilled reader will appreciate that such filter can be included at any suitable point in the path of the radiation. Alternatively or in addition, radiation source 11 itself may have switchable wavelengths, or multiple sources of different wavelengths can be provided.

The function of polarizer 12c in this example is performed by a polarizing beam splitter and combiner (PBSC) 134, which has an input face 136-S, 136-P for each path, and a single output face 138. Radiation emitted by output face 138 has the desired parameters of wavelength and polarization. Aperture device 13 lies behind output face 138 so as to impart a desired illumination profile to the radiation. Using the wheel form of aperture device, an open aperture 140 is shown in position, just for the sake of example. As shown in FIG. 6, any desired aperture can be put in this position, provided it is on the wheel.

The form and operation of polarizing beam splitters generally is well-known. Typically they comprise a cube having a splitting plane at 45 degrees. In the present example, PBSC 134 effectively comprises a modified cube (or a pair of cubes placed or joined side-by side), containing two partially reflecting surfaces 150 and 152. The cube material and surface coatings are specially designed to act as efficient polarizers, rather than simple reflectors. Neutral density filters 154 and 156 are provided to absorb light exiting faces of the modified cube that is unwanted light, in this application.

Figure 7A:
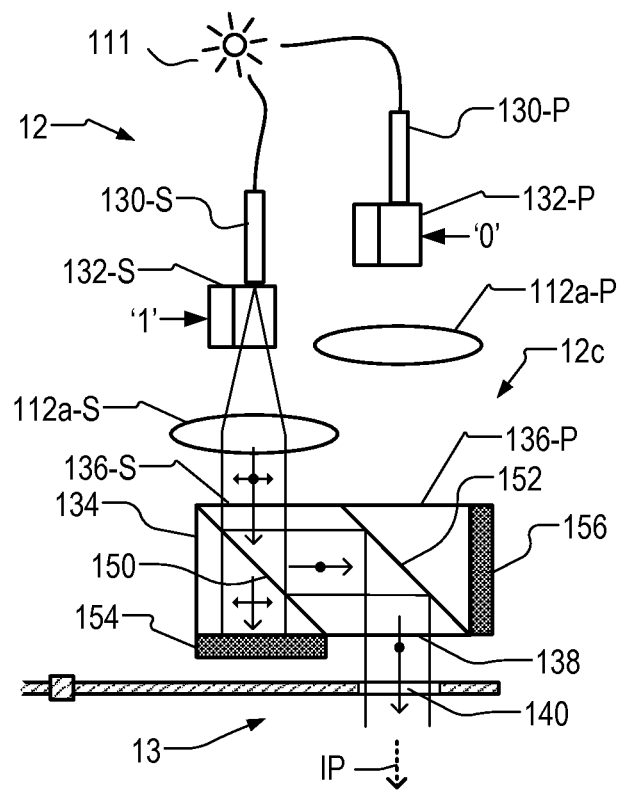
FIGS. 7a and 7b illustrate schematically the form and operation of the illumination system in the known inspection apparatus a when producing light with a first polarization direction and b when producing light with a second polarization direction.

Referring now to FIG. 7a, the operation of illumination system 12 in a first mode of operation is as follows. Suppose the metrology recipe specifies illumination parameters including a polarization direction into the plane of the drawing. For the purposes of this description, we will refer to this as the S direction. A control signal with value '1' is applied to shutter device 132-S to admit light from fiber 130S into the 'S' path, while a value '0' is applied to shutter device 132-P to block light from entering the 'P' path. It is assumed the light is unpolarized, although it could be pre-polarized if desired. Unpolarized light entering PBSC 134 at input face 136-S is reflected by surface 150 to become S-polarized, with respect to surface 150. The direction of polarization in this example is into the plane of the drawing, illustrated by the dot on the ray. P-polarized light, that is light polarized in the plane of the drawing, passes through surface 150 to be absorbed in ND filter 154. It is again reflected by surface 152 and leave PBSC 134 via output face 138. After passing through aperture 140, light with the desired set of illumination parameters enters the illumination path IP of the inspection apparatus.

Figure 7B:
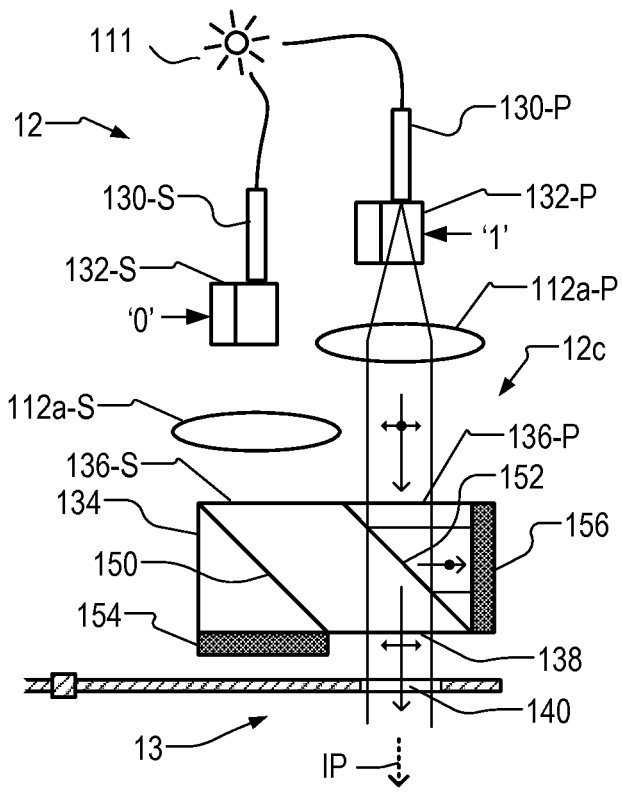

Referring to FIG. 7b, we suppose now that the metrology recipe is changed and illumination polarized in the plane of the drawing is desired, which we will call the P direction. The control signals of the shutter devices 132-S and 132-P are switched so that light from fiber 130-P can enter the 'P' path, while light is blocked from entering the 'S' path. Light with P polarization passes through surface 152 to leave PBSC 134 via output face 138, while light with S polarization is reflected an absorbed by ND filter 156.

Accordingly, by switching the control signals of the shutter devices 132-S and 132-P the polarization direction of radiation entering illumination path IP can be controlled. In a third mode of operation, both shutter devices can be opened, and both S- and P-polarized light included in the illumination. Assuming that source 11 is an incoherent source, this third mode provides effectively unpolarized light.

Compared with other types of polarizer, such as polarizing films, polarizing beam splitter devices offer very high polarizing performance. For example in commercially-available devices the 'extinction ratio' between the wanted/unwanted polarization directions can exceed 1000:1. As drawbacks of the known design, the mechanical components such as the shutter devices and the aperture wheel limit the speed with which illumination parameters can be switched. Also such mechanical devices are susceptible to vibrations in their operation, and can cause vibrations when switching. Additionally, the aperture wheel offers only a limited number of apertures and so restricts the range of metrology recipes that can be supported by the inspection apparatus.

It may be noted that the optical path length through PBSC 234 is longer for the 'S' path than it is for the 'P' path. It may be desirable to equalize the path lengths for a variety of reasons. Accordingly, a path length compensator such as a glass plate (not shown) can be included in the 'P' path, between SLM 260 and input face 236-P. This path difference may be important whenever the rays in each path are not parallel. This would apply particularly in an example where the device is being applied as a field stop 13', rather than a pupil stop.

Figure 8:
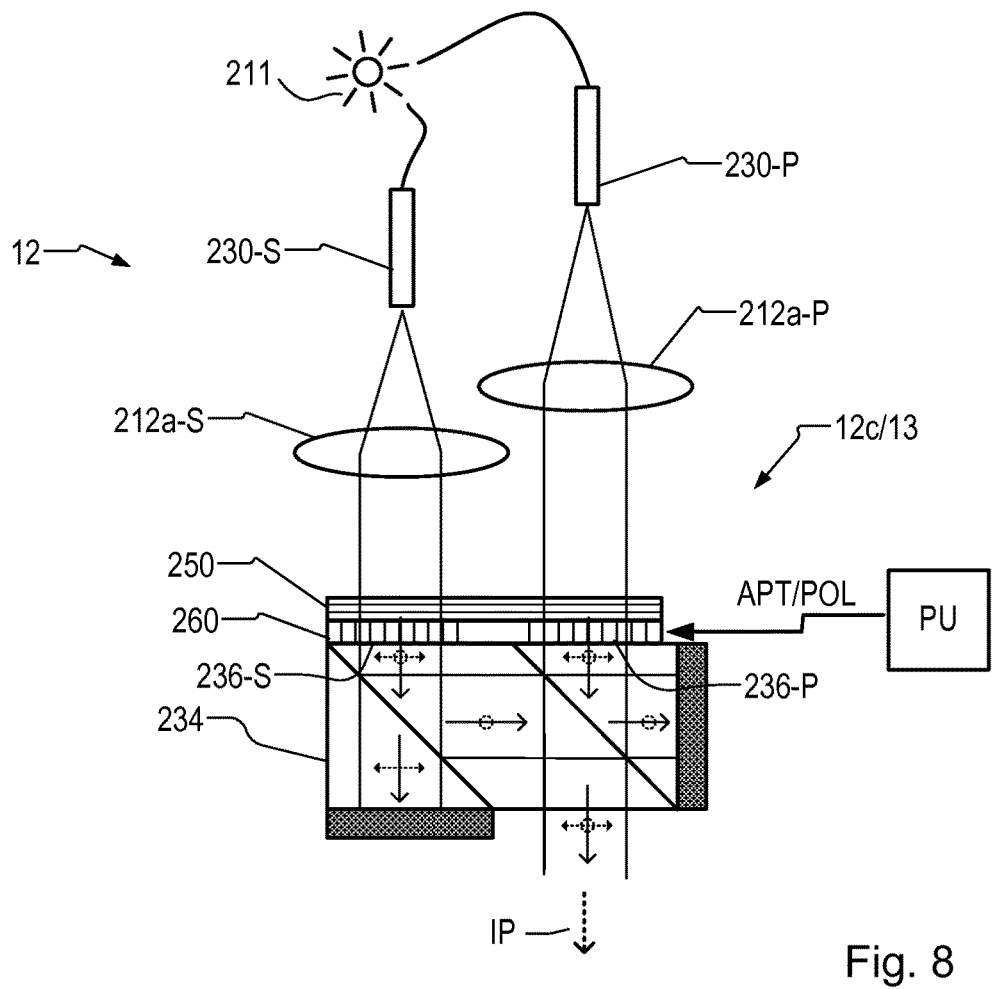
FIG. 8 illustrates schematically an illumination system with integrated selection of illumination profile and polarization according to a first embodiment of the present invention.

FIG. 8 shows a modified illumination system 12 according to one example of the present disclosure. Components having similar function to components in the known illumination system are labeled with similar reference signs, but with prefix '2'. Thus polarizing beam splitter and combiner (PBSC) is labeled 234. PBSC 234 has the same form as in the known illumination system of FIG. 7. On the other hand, an integrated polarizer and aperture device is formed by a combining PBSC 234 with a pre-polarizer 250 and a liquid crystal cell configured as a spatial light modulator (SLM) 260. Thicknesses of the various components are not to scale. SLM 260 comprises a number of active areas 262-S distributed across input face 236-S of PBSC 234 and another number of active areas 262-P distributed across the input face 236-P. SLM 260 can therefore be regarded as comprising or forming a first spatial light modulator supplying for example the 'S' path, and a second spatial light modulator supplying the 'P' path. Conveniently the two spatial light modulators are implemented side by side in a single device, but this is not essential.

SLM 260 is programmable so that optical properties of each active area controlled by a signal APT/POL received from a controller such as processing unit PU. As will be described in more detail below, the SLM 260 in this example is not a conventional SLM, but rather a spatial modulator of polarization. That is to say, SLM 260 can modify a polarization state of the transmitted light differently in different portions of the 'S' path. These different portions are determined by programming through signal APT/POL, which defines a first programmable pattern for active areas 262-S and a second programmable pattern for active areas 262-P.

These active areas can be envisaged most easily as square pixels in a two-dimensional array, and the term 'pixels' will be used for convenient in the following discussions. In other examples the active areas could take different forms, for example rings or ring segments centered on the optical axis. The term 'pixel' in the following examples should be understood as referring to an active area, regardless of its actual shape. The term 'array' should be understood as referring to the set of active areas distributed spatially over a certain plane in the illumination path, whether or not they are in a square or rectangular array or some other pattern.

Figure 9:
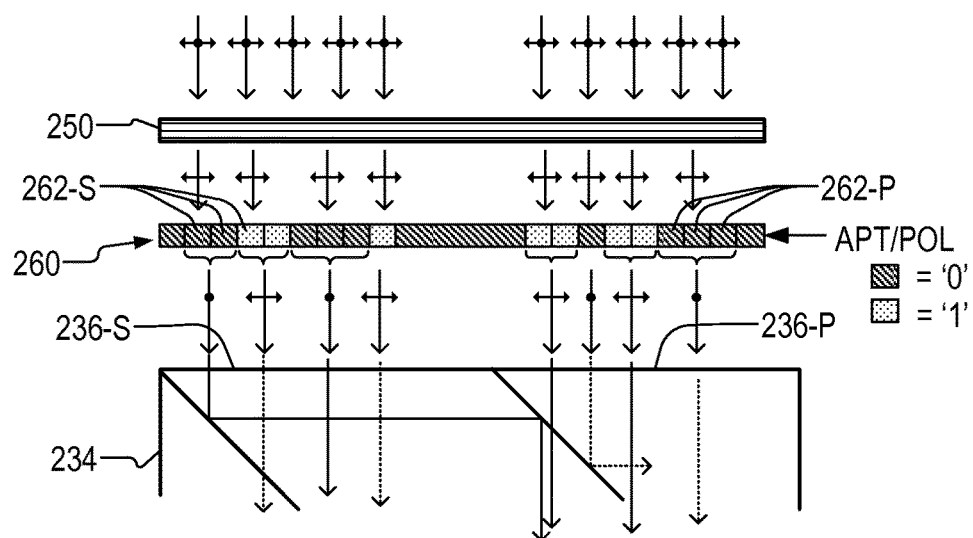
FIG. 9 illustrates in expanded detail the operation of the illumination system of FIG. 8.

FIG. 9 is an expanded view of the polarizer 250, SLM 260 and top part of the PBSC 234 in the illumination system of FIG. 8. These components can be formed and mounted separately as shown in the expanded view of FIG. 9. Conveniently, however, they are integrated into one more two blocks, as shown in FIG. 8. The light in the various parts of the apparatus is shown with polarization directions indicated. Pre-polarizer 250 imparts a single, uniform polarization direction (in this example the P direction) to the light as it approaches the active areas of SLM 260. The operation of the liquid crystal SLM in this example is such that an active area 262-S or 262-P controlled by a '0' (off state) value will twist (rotate) the angle of polarization of the light through 90 degrees as it is transmitted through SLM260. An active area controlled by a '1' value ('on' state) will not alter the polarization. Consequently, as illustrated in FIG. 9, for a subset of pixels 262-S that are at '0', light with S polarization will enter input face 236-S of PBSC 234. For the remaining pixels ('1'), P-polarized light enters input face 236-S. Because of the polarizing function of PBSC 234, only the S-polarized rays (solid lines) will be transmitted to the output face 238. Similarly, for a subset of pixels 262-P in the P-side of SLM 260 that are at '1', light with P polarization will enter input face 236-P of PBSC 234. Only these P-polarized rays will be transmitted to output face 238. For pixels 262-P that are at '0', rays will not be transmitted to the output face.

FIG. 10 shows the intensity and polarization illumination profiles 270 for six different illumination modes. These modes are selected by setting pixel values in SLM 260 to '0' or '1' via control signal APT/POL. In this simplified illustration, SLM 260 comprises two arrays of 4×4 pixels each. The illumination profile 270 therefore has a spatial resolution of 4×4 pixels, each of which can select/combine two polarization directions. When SLM 260 is deployed in a pupil plane of the illumination path, it performs in the role of aperture device 13. The square pixel array may cover the circular illumination pupil 272 of the inspection apparatus as shown by the dotted circle.

When SLM is deployed as a field stop 13' in a field plane (conjugate image plane), the square pixel array may cover a square image field, corresponding in size for example to the area of sensor 23. In the following examples, it will be assumed that the SLM is deployed as an aperture stop. The skilled person can readily envisage examples in which it the SLM 260 or equivalent part is deployed as a field stop 13', and such examples should be regarded as also disclosed herein, even when not mentioned explicitly. The SLM controls the polarization as well as the transmission or attenuation of radiation transmitted in each part of the field. Additionally, examples should be regarded as disclosed in which separate SLMs are deployed as aperture stop 13 and field stop 13'. Polarization behavior of the two SLMs in series should be taken into account in the design of such an example, however.

In FIG. 10 *a*, control signal APT/POL has value '0' for all pixels 262-S and 262-P. Referring again to FIG. 9, the result is that S-polarized rays are generated by SLM 260 at all pixels 262-S and 262-P. By the polarizing operation of PBSC 234, the 5-polarized rays from pixels 262-S are transmitted and those from pixels 262-P are blocked. The resulting illumination profile 270 is S polarized light across the whole pupil 272.

At b control signal APT/POL sets value '1' for all pixels 262-S and 262-P. Referring again to FIG. 9, the result is that P-polarized rays are transmitted by SLM 260 at all pixels 262-S and 262-P. By the polarizing operation of PBSC 234, the P-polarized rays from pixels 262-S are blocked and those from pixels 262-P are transmitted. The resulting illumination profile 270 is P polarized light across the whole pupil.

At c control signal APT/POL sets value '0' for all pixels 262-S and '1' for all pixels 262-P. The result is that S-polarized rays are transmitted by SLM 260 at all pixels 262-S and P-polarized rays are transmitted at all pixels 262-P. By the polarizing operation of PBSC 234, the S-polarized rays from pixels 262-S are transmitted and the P-polarized rays from pixels 262-P are transmitted. The resulting illumination profile 270 is a combination of S and P polarized light across the whole pupil. Assuming the source 211 is incoherent, the light may be regarded as unpolarized.

At d we see a combination of '0' and '1' values suitable to produce an illumination profile with dark and light quadrants, the light quadrants in this example having only S polarized light. By altering the values for each array of pixels 262-S and 262-P, different quadrants or other shapes can be freely illuminated with either or both S and P polarized light. At e we see two diametrically opposite quadrants having S polarized light and two intervening quadrants having P polarized light. As in the known publications, providing different qualities of light in different segments of the illumination pupil is one way of obtaining multiple measurements in a single operation. This can be useful for example in achieving the high throughput of measurements necessary for routine inspection in high-volume manufacturing.

Figure 10A:
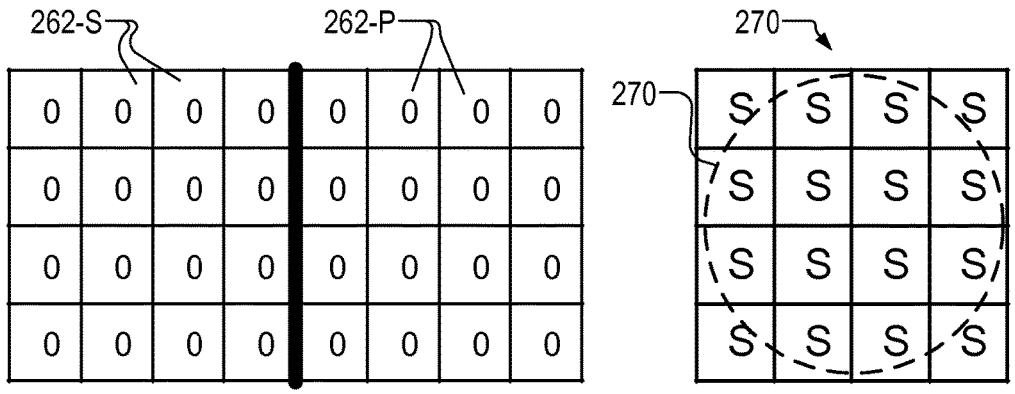
FIGS. 10a-10f illustrates at a to f the generation of different spatial illumination profiles and polarizations, using the illumination system of FIGS. 8 and 9.
Figure 10B:
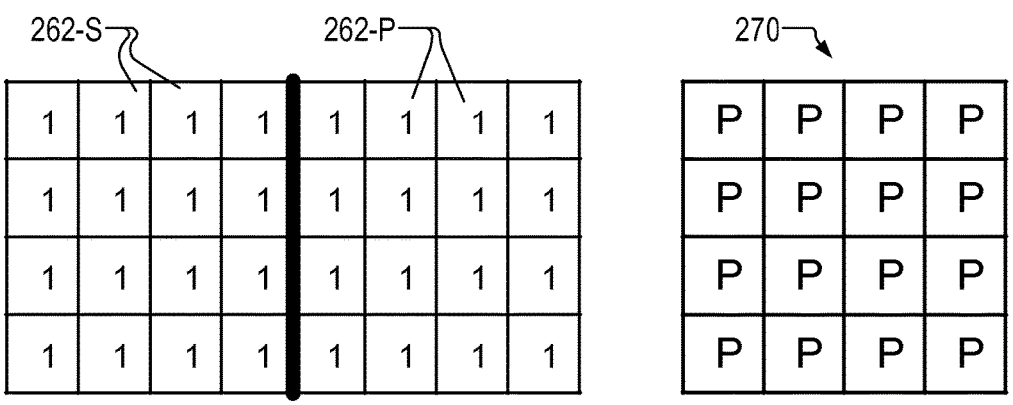
Figure 10C:
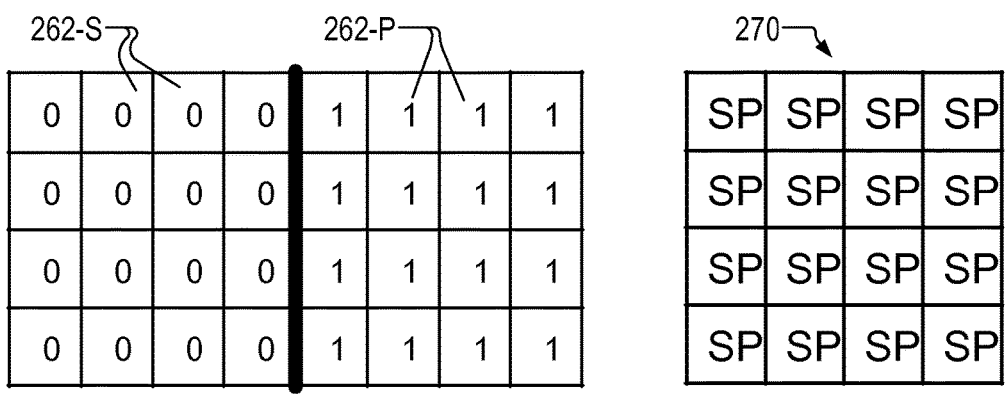
Figure 10D:
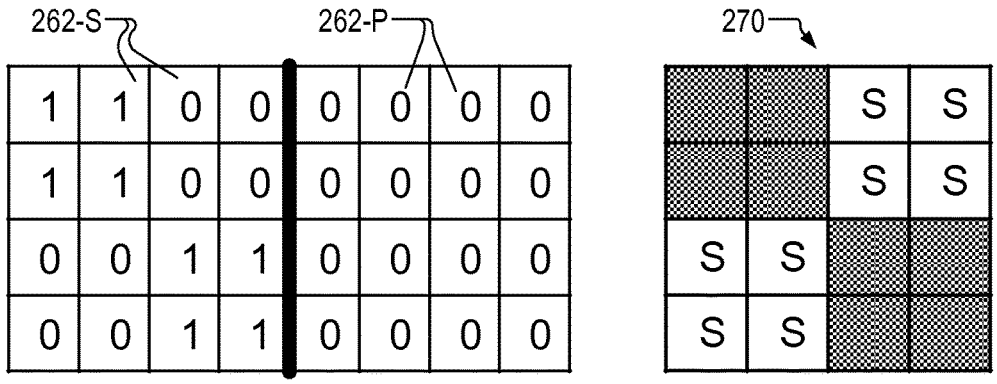
Figure 10E:
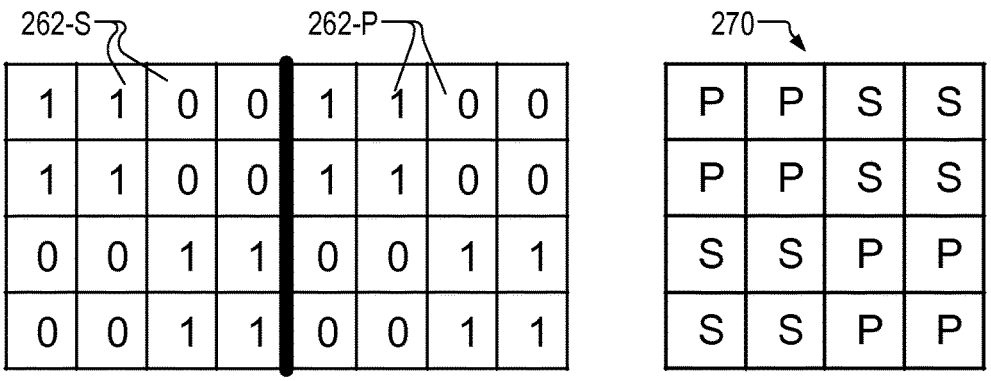
Figure 10F:
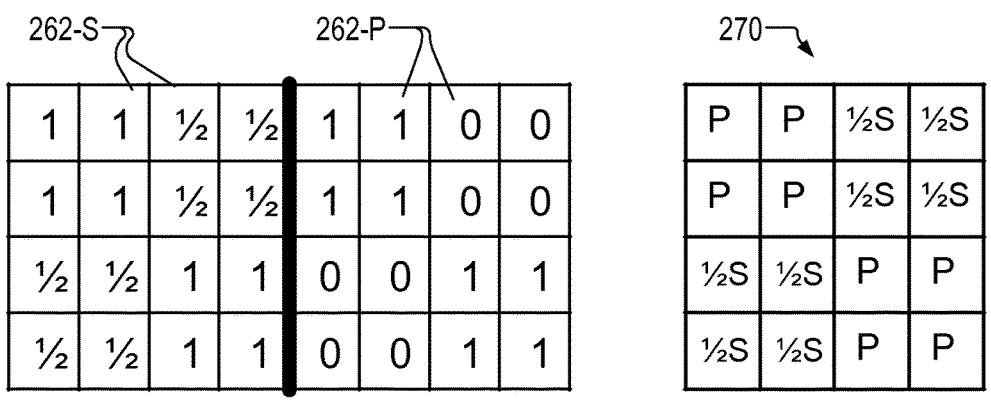

At FIG. 10*f* we see pixel values intermediate between '0' and '1', for some of the pixels 262-S. The intermediate value is represented by '½', just by way of example. In this example, the illumination profile comprises half-strength S-polarized light in two quadrants, and full strength P-polarized light in the other two quadrants. In other examples, a wider range of values can be set.

In FIGS. 9 and 10, only a few pixels are shown, for the sake of clarity. The number of pixels in a real implementation is of course a matter of design choice. There may be several hundred or many thousands of pixels in practice. For example, it may be convenient to provide a number of pixels in each path that is equal or substantially equal to the number of pixels in the pupil image sensor 19 of the inspection apparatus. In this way, spatial resolution in the illumination profile can match the spatial resolution in the pupil image sensor. For example there may be 500×500 pixels in each part of SLM 260 and 500×500 pixels in pupil image sensor 19.

At FIG. 10*f* we see pixel values intermediate between '0' and '1', for some of the pixels 262-S. The intermediate value is represented by '½', just by way of example. In this example, the illumination profile comprises half-strength S-polarized light in two quadrants, and full strength P-polarized light in the other two quadrants. In other examples, a wider range of values can be set, depending on the dynamic range of SLM 260. In addition to attenuating light of one polarization relative to the other (as shown in FIG. 10*e*), a particular application of intermediate values may be to incorporate an apodization function into the illumination system. Apodization filters are known in imaging optics and generally attenuate light toward the edges of the collection pupil. A similar function can be implemented in the illumination pupil 272 by feeding intermediate pixel values to SLM 260.

It will be recognized that these illumination modes and many more can be implemented using the illumination system of FIGS. 8 and 9. This system integrates in a single device the function of the aperture device 13 and the selection of other illumination parameters, such as polarization. The integrated device can be made compact if desired and contains no moving parts. Also the programmable SLM 260 can programmed with a far wider range of illumination profiles than the aperture wheel in the known apparatus of FIG. 7. The quality of polarization in the illumination path of the inspection apparatus can be maintained as in the known apparatus. In particular, where a polarizing beam splitter is used, the direction of polarization can be maintained as high as it was they are in the known instrument. The purity of polarization (extinction ratio of unwanted polarization in each ray) is dependent on the quality of the liquid crystal SLM 260 and the pre-polarizer 250.

The implementation shown in FIGS. 8 and 9 is not the only one possible and many variants can be considered. Already some variants have been mentioned above.

Figure 11:
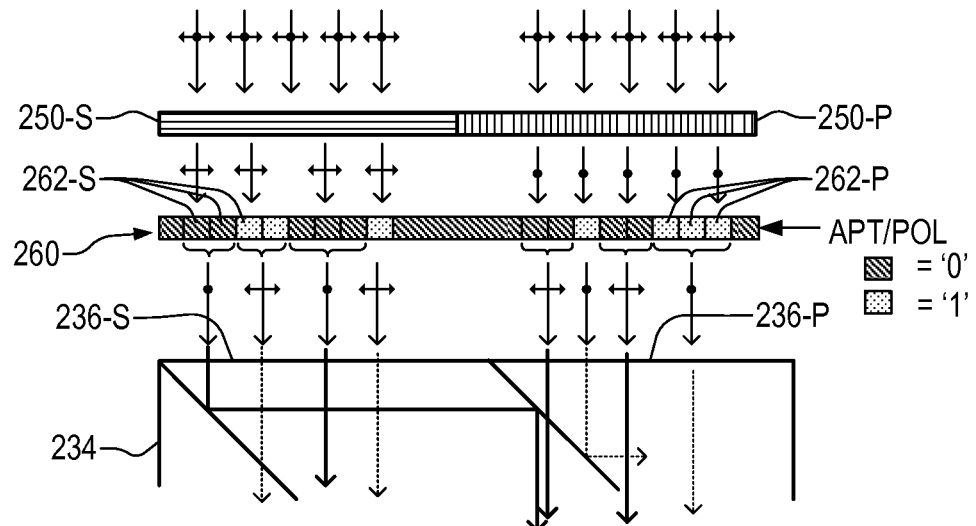
FIG. 11 illustrates in expanded detail the operation of the illumination system in a second embodiment.

FIG. 11 shows a simple modification of the FIGS. 8 and 9 example, in which pre-polarizer 250 has different polarization directions in the 'S' path and 'P' path. Recalling that SLM 260 will either twist or not twist the polarization of light transmitted by each pixel, the same illumination profiles can be obtained in this example as in FIG. 9, by inverting the values '0' and '1' in the 'P' array 262-P. This has the effect that '1' and '0' have the same "meaning" in the illumination profile, in both the 'S' and 'P' arrays.

Pre-polarizers 250 and 250-S/250-P have been shown as implemented with polarizing film material. In other examples, the pre-polarizing function can be implemented with more sophisticated polarizing elements, including for example a polarizing beam splitter in each path.

Figure 12:
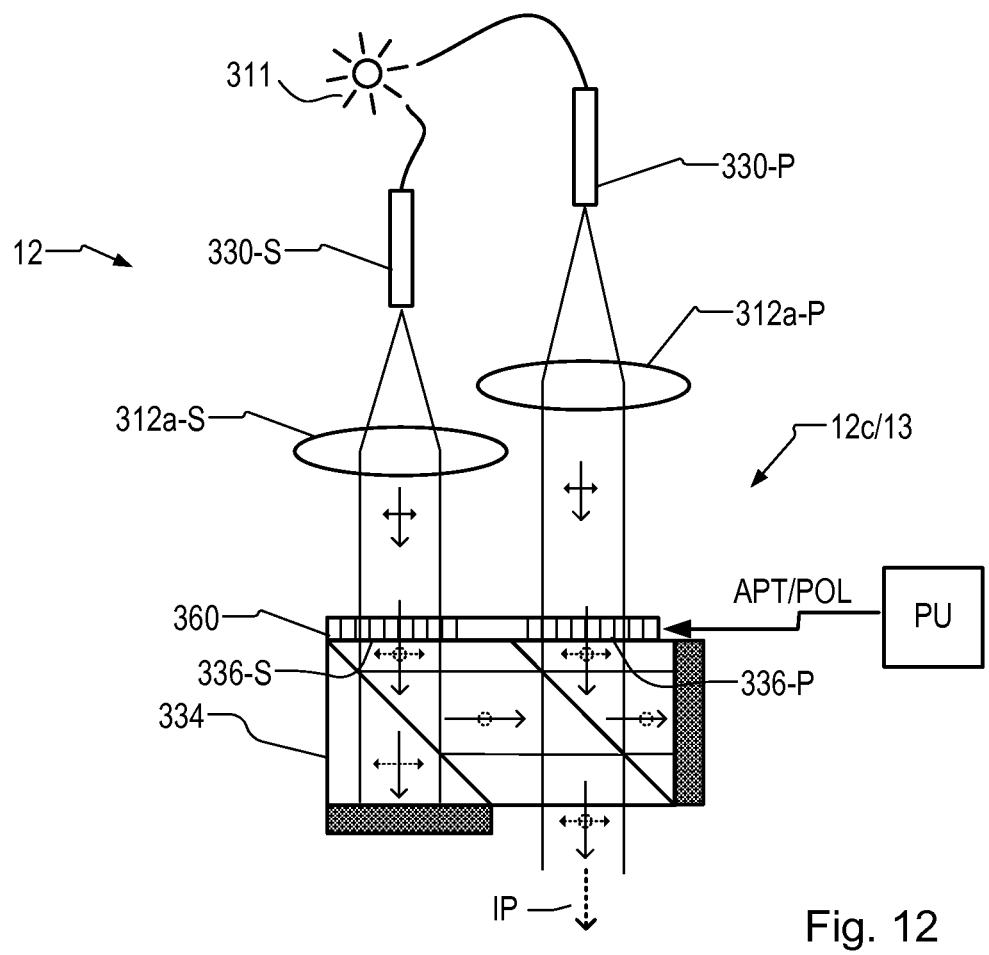
FIG. 12 illustrates schematically an illumination system in a third embodiment of the invention.

FIG. 12 shows an example in which components corresponding to those of FIGS. 8 and 9 are labeled with similar reference signs but with prefix '3'. A pre-polarizer like 250 is not present as a film at the input to SLM 360. Rather the light emanating from fibers 330-S and 330-P is already polarized, as shown. In the illustration, the light from both fibers is polarized in the plane of the drawing (P direction). The arrangement will function equally well with light from both fibers being polarized into the drawing (S direction), or with one S and one P. As explained already with reference to FIG. 11, the only adaptation required between these alternatives is in the meaning assigned to the '0' and '1' states of the pixels 262-S and 262-P. Note that polarization-preserving fibers are typically used with monochromatic light. In the case of a broadband light source, polarizing filters of some sort can be provide between the fiber ends and the SLM 360.

Figure 13:
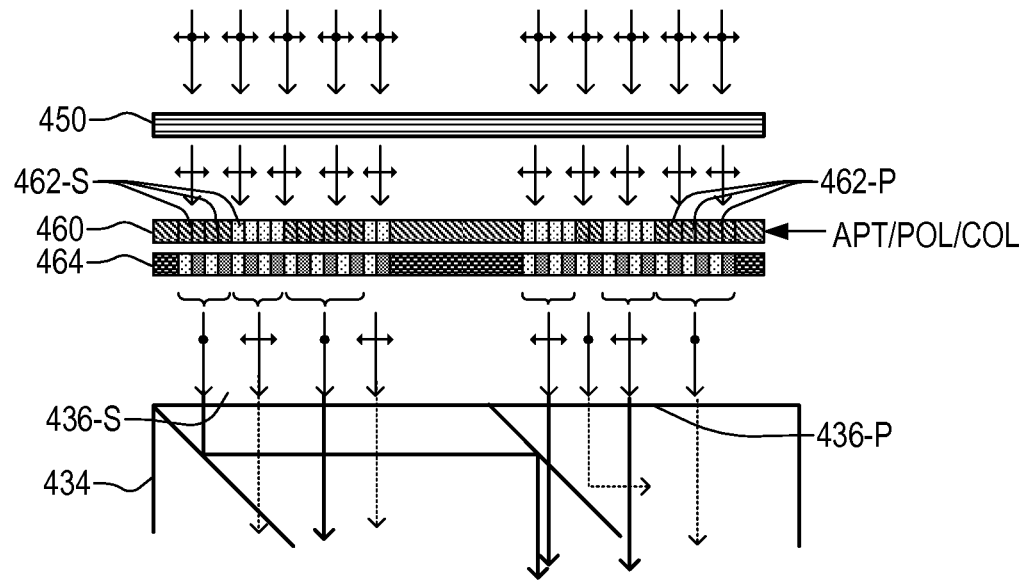
FIG. 13 illustrates in expanded detail the operation of the illumination system in a fourth embodiment.

FIG. 13 shows a modified example in which the wavelength or color of radiation at each pixel can be selected, as well as the polarization. Components having functions corresponding to like-numbered components in FIGS. 8, 9, 11, 12 and 13, are labeled with prefix '4'. The difference from previous examples is that a multi-colored filter 464 is provided in association with the SLM 460, so that each active area or pixel 462-S or 462-P has an associated color. In the cross section shown, alternating pixels have two alternating colors. In a two-dimensional array, three, four or more colors can be interleaved. For example pixels with red, green and blue filters may be provided, and/or pixels with an infrared filter. Such filters are well-known from camera sensors and LCD displays. While the color matrix filter 464 is shown behind SLM 460 in this example, of course it can be positioned in front. These elements are likely to be closely integrated with one another in practical embodiment. The provision of a color matrix can be implemented in any of the examples disclosed herein.

In order to preserve spatial resolution, the individual pixels may be made smaller. As will be appreciated, this example gives the flexibility of switching colors and polarization without the problem associated with moving filter parts. On the other hand, the size of each pixel is smaller and so it may be more challenging to deliver a desired quantity of light for a accurate measurement. Examples of customized color and polarization profiles are disclosed in another published patent application US20130141730A1. The customized profiles in that case are achieved by switching different colors and polarizations of light between different fibers of a fiber bundle, the ends of the fibers being distributed spatially across the illumination pupil plane.

Figure 14:
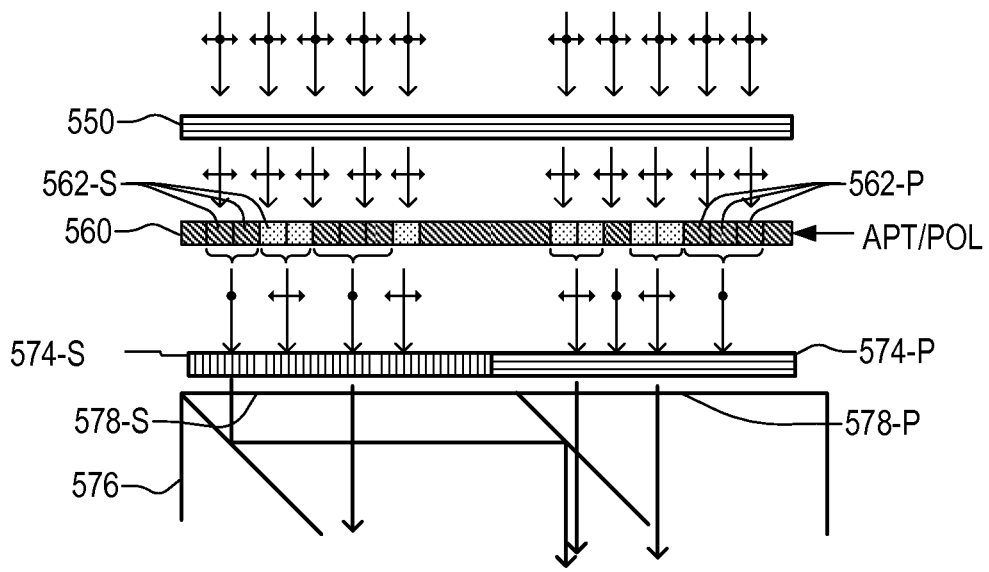
FIG. 14 illustrates in expanded detail the operation of the illumination system in a fifth embodiment.

FIG. 14 shows a modified example in which polarizing beam splitter and combiner 234 is replaced by film-type polarizers serving as analyzers 574-S 60 and 574-P and a separate beam combiner 576. Other components have functions corresponding to like-numbered components in FIGS. 8, 9, 11, 12 and 13, but are labeled with prefix '5'. Pre-polarizer 550 has a uniform polarization direction across both 'S' and 'P' paths, but could equally have different polarizations, for example as shown in FIG. 11. In the 'S' path, rays from pixels 562-S where polarization is twisted by SLM 560 are transmitted by analyzer 574-S, while rays from other pixels are blocked. In the 'P' path, rays from pixels 562-P where polarization is twisted by SLM 560 are blocked by analyzer 574-S, while rays from other pixels are transmitted. Beam combiner 576 does not need to implement an analyzer function, although if it has polarization selectivity, the purity of the polarization entering illumination path IP may be enhanced. Again, equivalent behaviors can be obtained with different polarization directions in the pre-polarizer(s) 550 and analyzers 574-S, 574-P, provided that appropriate attention is paid to the meaning of '0' and '1' control values for SLM pixels 562-S and 562-P. Pre-polarizer 550 can be implemented other than by films.

Figure 15:
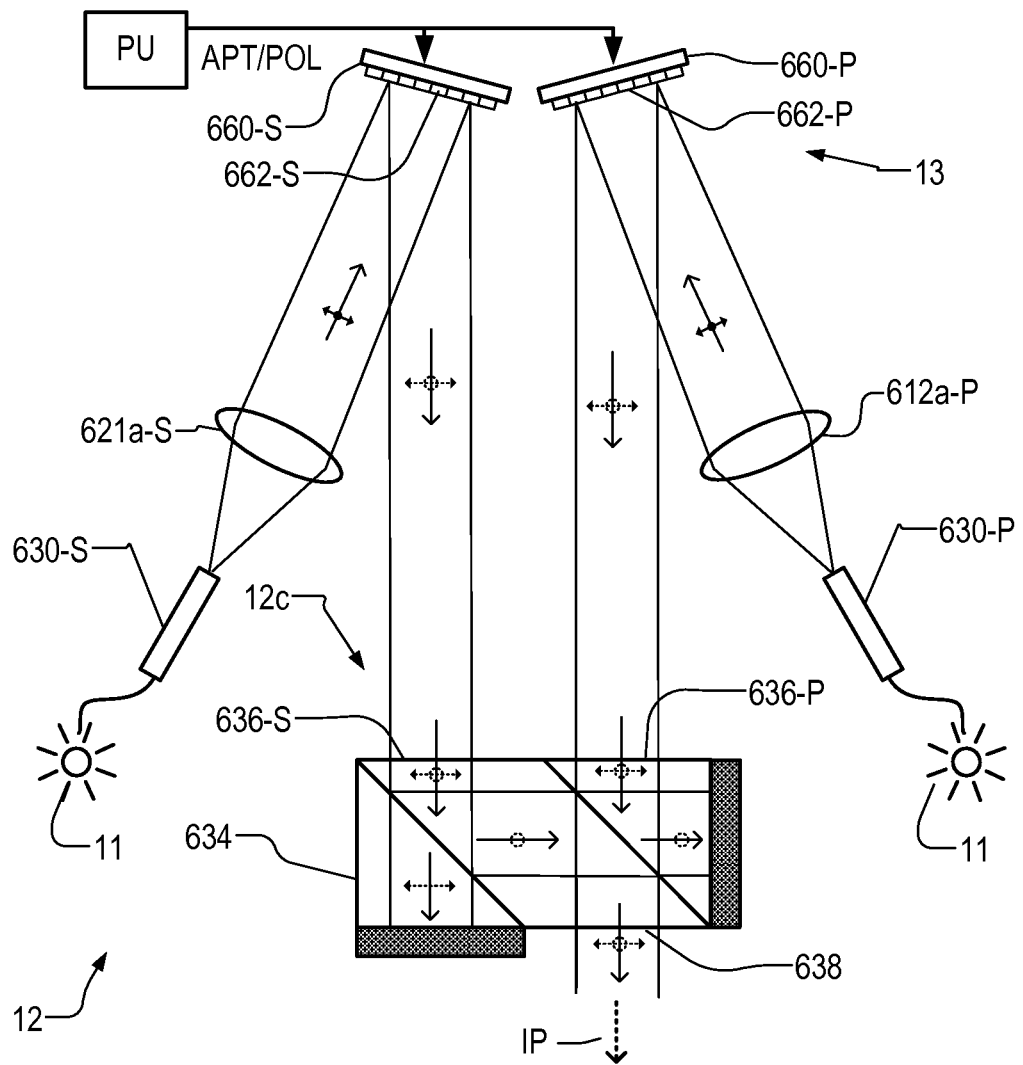
FIG. 15 illustrates schematically an illumination system in a sixth embodiment.

FIG. 15 shows a modified example in which spatial light modulator serving as aperture device 13 (or field stop 13') is of a reflective type. Reference signs in this example have prefix '6'. Accordingly, instead of a liquid crystal or other transmissive type of SLM, a reflective SLM 660-S is provided in a first ('S') path leading to the first input face 636-S of PBSC 634. A second reflective SLM 660-P is provided in a second ('P') path leading to second input face 636-P of PBSC 634. Each SLM, which may for example be a deformable micromirror device (DMD) has an array of pixels 662-S or 662-P that may be controlled individually to direct light to PBSC 634 or not, according to a desired illumination profile. A reflective SLM will not normally have the effect of modulating polarization, but rather directs the light into the path or not, according to the '0' or '1' value controlling it. Accordingly, in this example, no pre-polarizer is necessary as only the correct polarization for the rays from '1' pixels in each path will be transmitted through PBSC 634 into the illumination path IP. Pre-polarizers could optionally be provided, however. They can be located anywhere in the path between source 11 and the respective input faces 636-S and 636-P of PBSC 634.

As in the case of transmissive SLM examples discussed above, many variants are possible. While the SLMs 660-S and 660-P are shown as separate devices, a different optical layout can be envisaged in which the array of pixels 662-S and the array of pixels 662-P are different parts of a single array on a common substrate. While the drawings are necessarily restricted to schematic illustrations in two-dimensions, the real design can take advantage of the third dimension to achieve a practical layout of the various components and beam paths.

Figure 16:
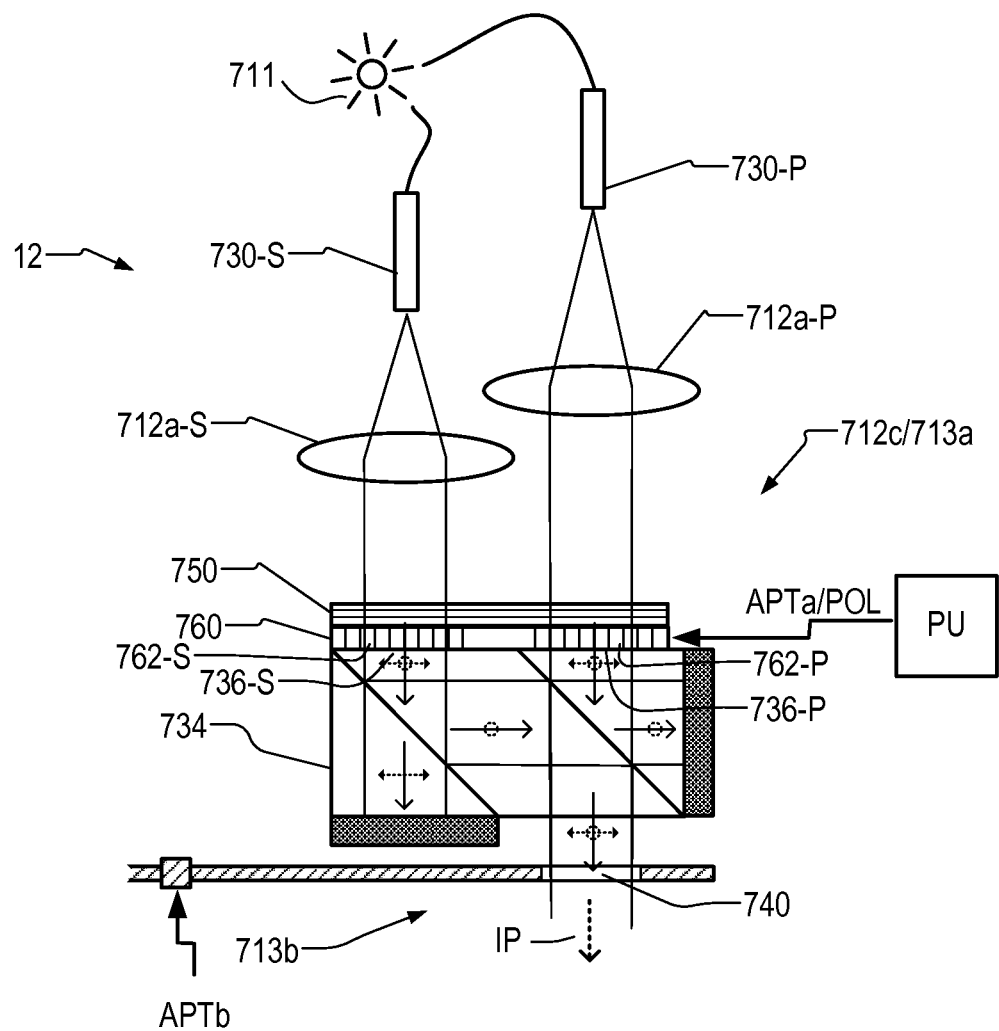
FIG. 16 illustrates schematically an illumination system in a seventh embodiment.

FIG. 16 illustrates another variation that can be applied in any of the examples above. In this example, prefix '7' is applied to the reference signs. The spatial distribution of light in the illumination path is controlled partly by the SLM 760 and PSBC 734, and partly by a more conventional aperture 740, provided for example on an aperture wheel. SLM 760 effectively forms a first part 713a of the aperture device 13 (or field stop 13'), while an aperture wheel forms a second part 713b. Aperture 740 is shown downstream of PBSC 734 for convenience in the drawing. It may be provided upstream, for example to get closer to the plane of SLM 760. In that case, however, a pair of apertures (740-S, 740-P) will be needed.

Each type of device 740, 760 can be used to perform a different function. For example, SLM 760 may be effective at applying fine detail within the aperture, but with imperfect extinction of light in the 'dark' areas. Aperture 740 in that case may comprise a few coarse aperture patterns with very high attenuation, to block light more effectively in areas where fine detail is not important.

As another example, fine detail with good extinction can be provide by aperture 740, while polarization is controlled by SLM760. In such a case, it may be acceptable for SLM 760 to have a few coarse active areas. For example, the desired illumination profile may require a precisely defined bright area in a given quadrant or half of the pupil (or field), but, within that area, only one type of polarization is required. The active areas 762-S and 762-P in that case could comprise whole quadrants. Of course, the problem remains in that case that the use of an aperture wheel limits the number of patterns available for choice.

As another example, where an apodization function is desired, it may be preferred for practical reasons to implement this in one of the SLM 760 or aperture 760, while other aspects of the illumination profile are implemented in the other.

Figure 17:
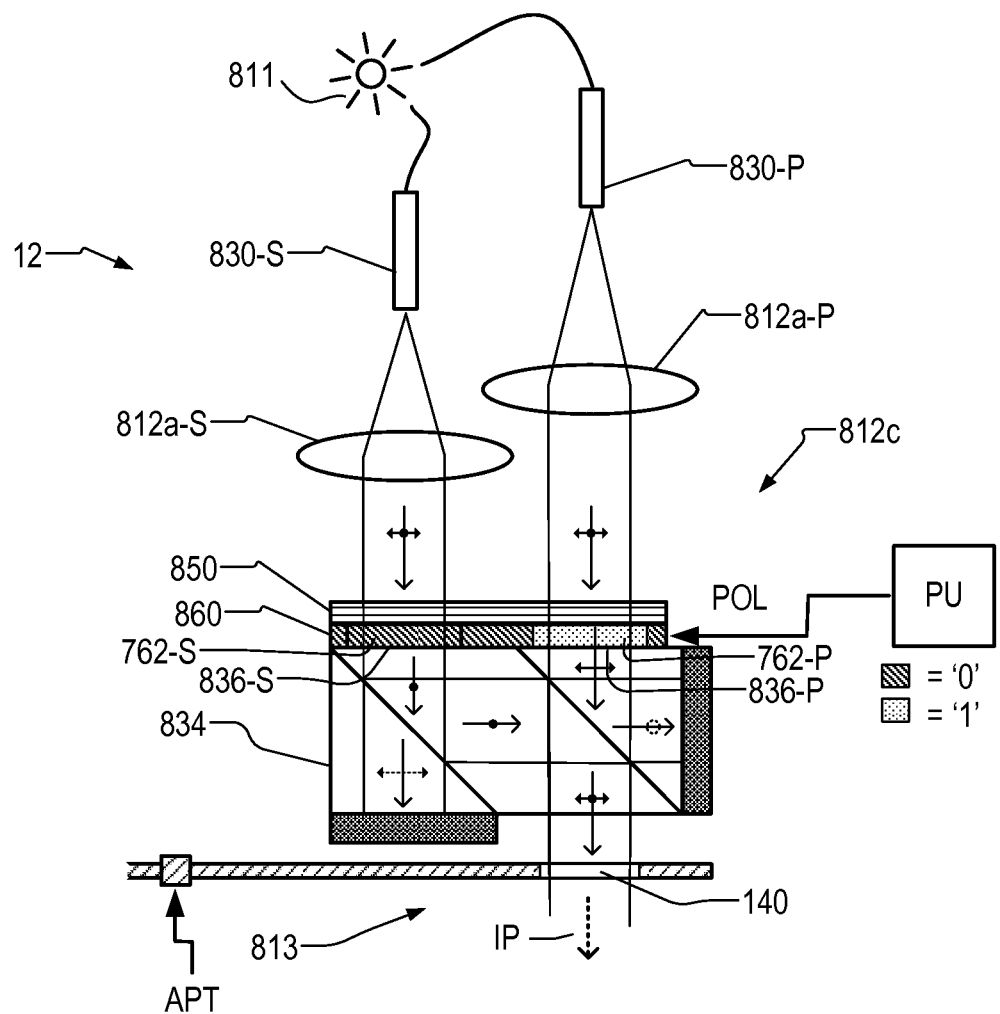
FIG. 17 illustrates schematically an illumination system in an eighth embodiment.

FIG. 17 shows another example, in which reference signs have prefix '8'. This example is similar to that of FIG. 16, except that the active areas 762-S and 762-P have no spatial division at all. In that regard, the SLM 860 and PBSC 834 function as a polarization selector with no spatial modulation. SLM 860 in this extreme example is only a spatial light modulator in the sense that the two paths 'S' and 'P' are spatially separated. There is no spatial modulation within the pupil (or field). The pre-polarizer 850, SLM 760 and PBSC 834 function similarly to the arrangement shown in FIG. 7, but with the benefit of eliminating the moving parts of shutter devices 132-S, 132-P. The LC cell is illustrated in the state where both S and P polarized radiation is delivered to illumination path IP. Such an example may be applied in situations where spatial variation of polarization is not required, and where a few apertures 740 are sufficient. On the other hand, it is very easy to adapt the SLM 860 to include at least four active areas 862-S and 862-P. This will give additional benefits of being able to select different polarizations. In all of the examples described above, it is assumed that light entering the 'S' and 'P' paths is incoherent. In a modified example with coherent radiation in the 'S' and 'P' paths, depending on the relative phase of the radiation, the 'SP' illumination mode of FIG. 10c may contain linear polarization with a 45 degree orientation, or elliptical or circular polarized radiation. Phase shifting plates can be included to select between these types of polarization as a further illumination parameter, if desired.

Figure 18:
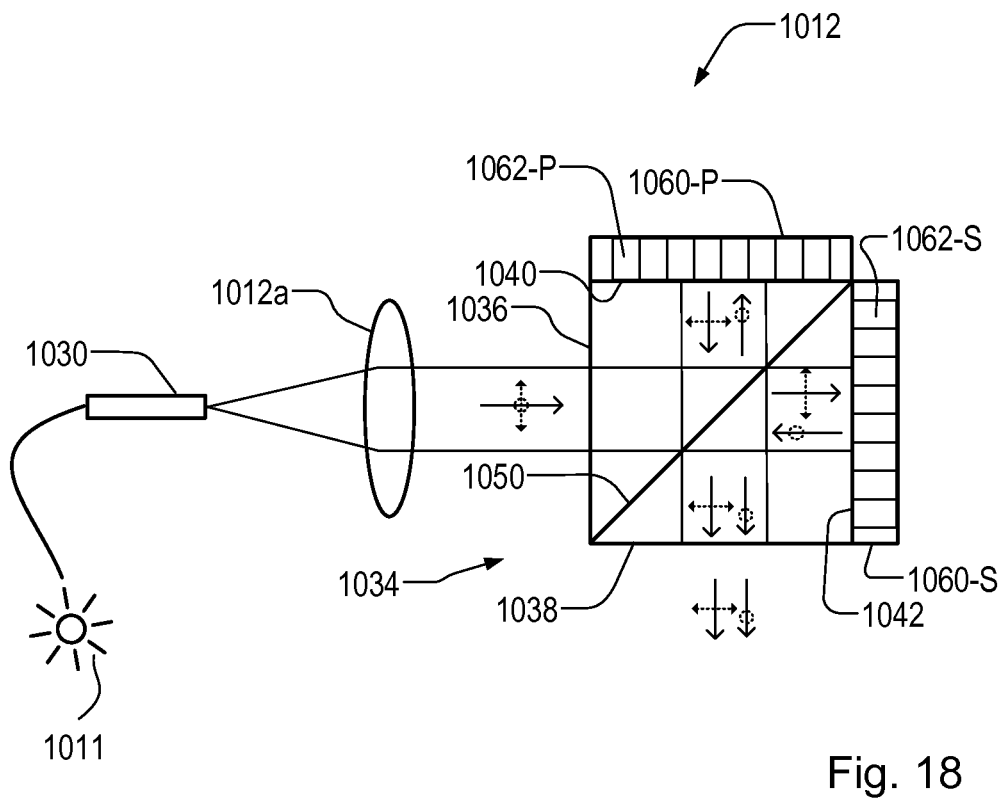
FIG. 18 illustrates schematically an illumination system according to a ninth embodiment.

FIG. 18 shows a modified illumination system 1012 according to another example. Components having similar function to components in previously mentioned illumination systems are labelled with similar reference signs, but with prefix '10'. A polarizing beam splitter & combiner (PBSC) is for example labelled 1034. Light in the various parts of the system is shown with polarization directions indicated.

PBSC 1034 has an input face 1036 and an output face 1038. The input and output faces are adjacent in the present example, where they were opposite in the previous examples. PBSC 1034 has a single partially reflecting internal surface 1050. (We refer to a 'single' surface only by way of contrast with the previous examples which have two surfaces. The surface 1050 may in itself comprise a multi-layer structure.) A first spatial light modulator 1060-P is located at a third face 1040 of PBSC 1034 such that light from input face 1036 that is reflected at internal surface 1050 will hit reflective SLM 1060-P. A second spatial light modulator 1060-S is located at a fourth face 1042 of PBSC 1034 which is opposite input face 1036 such that light transmitted through surface 1050 will hit SLM 1060-S. SLM 1060-P is of a reflective type in this example, and comprises a number of active areas 1062-P. SLM 1060-S similarly is of a reflective type in this example and comprises a number of active areas 1062-S. SLMs 1060-P and 1060-S are programmable in a manner similar to SLM 260, as described above.

In one example, one or both of the reflective SLMs 1060-P and 1060-S is a reflective liquid crystal (LC) cell, which is itself reflective or has a reflective backing. These LC cells may be for example reflective Liquid Crystal on Silicon panels. Further examples of suitable LC cells include an ordinary amorphous silicon active matrix LCD, or passive matrix LCD. The liquid crystal effect employed by the LC cells may be one of: twisted nematic, super-twisted nematic, vertically aligned, or cholesteric, or may be any other suitable liquid crystal effect. The LC cell may additionally comprise retarder foils to enhance the performance. It will, however, be appreciated that other types of LC panels exist that may be applied to modify polarization of the incoming light as described in the following. For the present application, both SLMs are expected to have the same construction and manner of operation, but in principle they could be different.

In this example, an active area, or 'pixel' (as discussed above), 1062-P or 1062-S controlled by a '1' ('on' state) value will rotate the angle of polarization of reflected light through 90 degrees, relative to light incident on the SLM. An active area controlled by a '0' value ('off' state) has a different behavior. Depending on the implementation, a pixel in the 'off' state may either not alter the polarization or not reflect any light. Where the active area does not alter the polarization when in an off state, the reflected radiation will be blocked by the PBSC 1034, rather than being delivered to output face 1038. Thus, SLM 1060-P and SLM 1060-S function in a manner similar to SLM 260-S and 260-P described above, except for SLM 1060-P and 1060-S reflecting the incoming radiation rather than transmitting the incoming radiation.

The operation of illumination system 1012 is as follows. Light from radiation source 1011 can include both S- and P-polarized light. Radiation source 1011 may additionally have switchable wavelengths, or multiple sources of different wavelengths can be provided. It passes through fiber 1030 and collimating lens system 1012a, and enters PBSC 1034 through input face 1036. Incoming S-polarized light from light source 1011 is reflected at surface 1050, whereas P-polarized light passes through surface 1050. The operation of SLM 1060-P is such that an active area 1062-P in an 'on' state will rotate the angle of polarization of the light through 90 degrees as it is reflected by SLM 1060-P. Thus, light will be reflected and rotated only by a subset of pixels 1062-P that are in the 'on' state. For the remaining pixels (in an 'off' state), no light is reflected, or the light is reflected with unchanged polarization. The incoming S-polarized light, following rotation through 90 degrees, is reflected as P-polarized light. The reflected P-polarized light can then pass through surface 1050 and exit the PBSC 1034 through output face 1038. Similarly, incoming P-polarized light from light source 1011 passes through surface 1050 of PBSC 1034, as only S-polarized light is reflected by the surface. The incoming P-polarized light is reflected by the subset of pixels 1062-S that are in the on state. Further, the incoming P-polarized light will be converted into reflected S-polarized light, where a pixel is in the 'on' state. The reflected S-polarized light is reflected by surface 1050 and exits the PBSC 1034 through output face 1038.

By this mechanism, partially reflecting surface 1050 performs not only the function of beam combiner (as in the previous examples), but also the functions of first and second pre-polarizers. The third face 1040 of PBSC 1034 not only provides a first input path for spatially modulated first radiation to be combined into the output path, but also delivers pre-polarized first radiation to illuminate the first SLM 1060-P. Similarly, the fourth face 1042 of PBSC 1034 not only provides a second input path for spatially modulated second radiation to be combined into the output path, but also delivers pre-polarized second radiation to SLM 1060-S. The construction is thus more compact and simplified, relative to the previous examples. The illumination system of FIG. 18 can be used to provide desired illumination profiles in a scatterometer or any of the applications mentioned for the previous examples.

Figure 19:
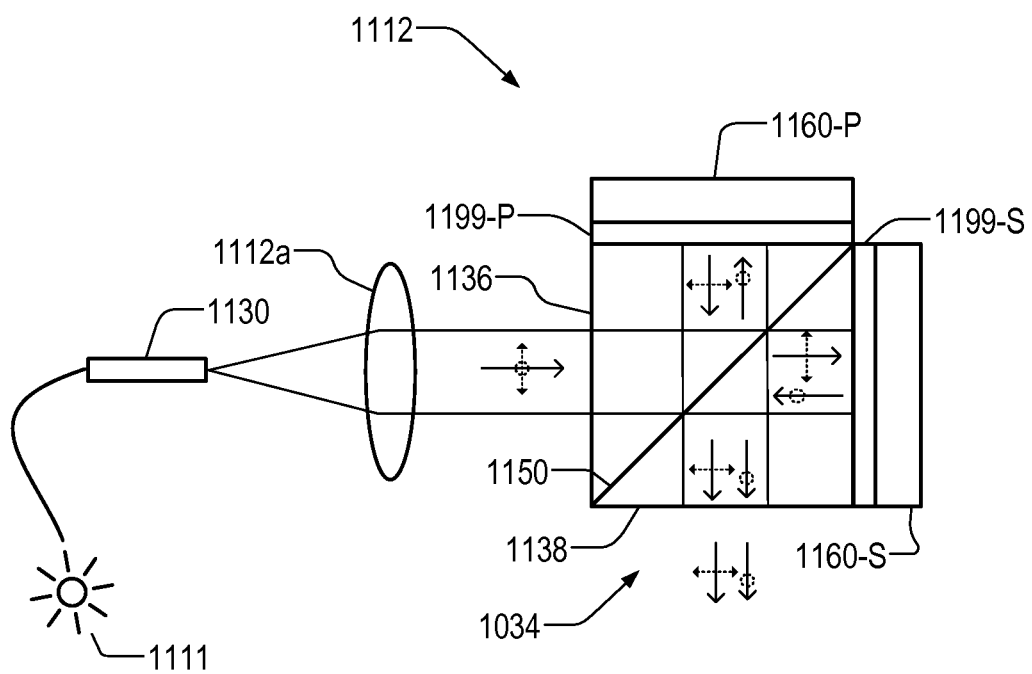
FIG. 19 illustrates schematically an illumination system according to a tenth embodiment.

FIG. 19 shows a modified illumination system 1112 according to a third example of the present disclosure. Components having similar function to components in previous examples are labeled with similar reference signs, but with prefix '11'. The illumination system 1112 in the third example is substantially identical to that described in the second example above, except for the differences described in the following.

In this example first and second SLMs 1160-P and 1160-S are programmable two-dimensional arrays of switchable reflective elements. Suitable devices are commonly available in the form of 'Digital Micromirror Device' (DMD). However, in principle, the reflective SLMs 1160-P and 1160-S could be implemented by other suitable types of programmable reflective components.

Each of the reflective elements (pixels) in each SLM can be switched between an 'on' state in which the element reflects light, and an 'off' state in which the element does not reflect any light, or alternatively reflects the light in a direction outside the acceptance angle of the system. While the array of reflective elements is shown parallel against the face 1040, 1042 of PBSC 1034, a practical embodiment may require the array to be at an angle, depending on the orientation of the reflective elements in the 'on' state. The illustration here is purely schematic.

A polarization modifying element 1199-P, 1199-S is provided in front of each of the SLMs 1160-P and 1160-S. By passing the radiation twice through this element, radiation reflected by the 'on' pixels will be delivered into PBSC 1034 with a polarization 90° rotated. In one example, element 1199 is a 'quarter wave' plate. A quarter-wave plate, which may be made by a stack of 'retarder film', will transform linearly polarized light into circularly polarized light and vice versa, in a manner well-known in the art. By passing radiation twice through the quarter wave plate, the result is a 90° rotation of linear polarization.

The operation of the illumination system 1112 is analogous to that of the second example of the present disclosure, as described above, except for the following differences. Incoming light (which may be unpolarized or elliptically or circularly polarized) is split into different polarized components, which are respectively reflected or transmitted by surface 1150. Each of these components (first and second radiation) passes through the element 1199-P or 1199-S. If the relevant reflective elements are in an on state, the incoming light is reflected and passes through the element a second time. In the instance of the element being a 'quarter wave plate', the incoming light is converted from linearly polarized light into circularly polarized light when passing through the element. The circularly polarized reflected light is converted back into linearly polarized light by the second pass through the element, but with the polarization direction of the reflected light rotated through 90 degrees compared with the incoming light. Thus, each of the SLMs 1160-P or 1160-S, when acting in unison with the element 1199, has functionality analogous to that of the SLMs 1060-P and 1060-S respectively.

In the examples described above, spatial modulation is performed in two paths, each having a different character of light. Selecting to use light from one or the other or both of these paths at each pixel location allows a spatial illumination profile to be defined at the same time as selecting or blending between two values of an illumination parameter for that profile. Further embodiments are possible in which the character of light in one or both paths can be adjusted as a further illumination parameter. For example, wavelength (color) of light can be made different between the paths. Thus more than two values of the illumination parameter can be selected or blended. Moving parts may be provided in one or both paths to achieve the adjustment. Alternatively, the color matrix filter of FIG. 13 can be employed.

In the examples described above, spatial modulation is performed in two paths, each having a different character of light. Selecting to use light from one or the other or both of these paths at each pixel location allows a spatial illumination profile to be defined at the same time as selecting or blending between two values of an illumination parameter for that profile. Further embodiments are possible in which more than two paths having different characters of light are defined, each has a programmable spatial light modulator. For example a first pair of paths may have the same type of polarization but two different wavelengths, while a second pair of paths have another type of polarization and the same two different wavelengths. Combining the four paths into one illumination path IP allows the spatial illumination profile and values of the other illumination parameters (polarization, wavelength) to be selected or blended.

In the examples above, the pattern of active areas (pixels) is the same in both paths (or in all paths). In principle this need not be the case. For example, different spatial resolutions or different shapes of active areas may be appropriate for use with different wavelengths, or different polarizations.

The spatial light modulators may allow for 'gray scale driving', i.e. allowing individual pixels of the spatial light modulators to reflect or transmit only a portion of the incident light. This could, for example, be achieved by controlling the polarization rotation angle (in an LC cell), controlling the reflection amplitude, or by pulse width modulation (in a digital mirror device). There are of course other methods for driving the pixels of the spatial light modulators, dependent on the type of modulators used.

In the examples above, radiation source 11, 1011, 1111 is a single source shared (split) between the two (or more) paths, for example using optical fibers. In alternative examples, separate sources may be used for the two paths. In the example of FIGS. 18 and 19, the radiation from source 1011, 1111 is delivered via a single fiber (or other delivery system) to input face 1036 of PBSC 1034. The source radiation is split into two polarized components only when it reaches the partially reflecting surface 1050 within PBSC 1034.

In the example SLMs above using liquid crystal cells, a direction of linear polarization is twisted or not twisted by each active area, depending on the programmed pattern. A twisted nematic or super-twisted nematic LC cell can be employed. Other types of liquid crystal material are of course known and may be applied to modify polarization in a different way, and/or to achieve faster switching times. While the examples described above can be implemented by simple electrically-addressed SLMs, optically addressed SLMs are also known, and may be employed if desired. Optically addressed SLMs may be used, for example, to obtain faster switching times. Reflective SLMs based on liquid crystals are also known, including optically-addressed SLMs and so-called liquid crystal-on-silicon (LCoS) displays. These may be applied in a layout similar to that shown in FIG. 15, 18 or 19.

Where linear polarization has been described, circular polarization can be applied and controlled by different types of LC material. Even with linear polarization, the polarization direction does not need to be the same across all active areas. For example, so called radial or tangential polarization modes have been used in some types of inspection apparatus.

The examples above enable a range of possibilities for increasing the performance of an illumination system, such as, but not necessarily limited to, the following.

In an inspection apparatus such as the scatterometer of FIGS. 3 and 4, flexibility in setting the aperture shape can be used to illuminate only those parts of the pupil that generate (for example) 1st order diffraction signals from a given target and that can be captured. This limits the amount of irrelevant light in the optical system, and thus reduces stray light and ghosts.

There is flexibility in setting of the polarization ratio, i.e. the ratio between P-polarized light and S-polarized light. This flexibility implies that tool-to-tool differences in the polarization ratio can be calibrated out. In systems which use a 'mixed' polarization mode, the polarization ratio may vary from tool to tool. 'Gray scale driving', as described above, can be used to correct for this.

Aperture shape and polarization ratio per SLM pixel position can be optimized in order to maximize the stack sensitivity and optimize measurement performance. This optimization procedure can be performed before each measurement, or once per wafer, once per lot, or even more once during recipe set-up for a new product, or during calibration of the inspection apparatus.

System asymmetry can be measured per pixel position by selectively activating each pixel in the aperture shape. This measurement can be made using a dummy target, a dedicated calibration structure, or on a 'real' target, such as one of the metrology targets or target gratings T described herein. Measured asymmetries can then be corrected, by modifying the intensities of the pixels to compensate for asymmetries in the source distribution or sensor symmetry. This new method would not just measure the asymmetry and calculate it out afterwards, but really correct it during subsequent measurements. This can dramatically reduce the sensitivity to process variation and reduce the tight requirements on the rest of the system.

By measuring at multiple pupil shapes the angle dependence of the target response can be measured. This can help to identify grating asymmetries that could compromise the measurement accuracy. Although this might be time consuming, it could be used for example during recipe set-up to identify the settings that are least sensitive to target asymmetry. In this way the accuracy of the measurement in high volume manufacture can be improved.

An illumination system as provided in the above examples would preferably be equipped with an optimization procedure to find the most optimum settings.

CONCLUSION

The inspection apparatuses disclosed herein enable the design and use of metrology recipes with greater freedom than existing systems, and can eliminate sources of delay and/or error that are associated with mechanical switching of illumination parameters and illumination profiles. Optimized illumination recipes allow better metrology performance, whether in scatterometry, diffraction based metrology, dark-field imaging metrology or other techniques. Improved speed of switching between illumination recipes allows certain types of measurement to be undertaken more quickly, particularly when a single measurement such as asymmetry requires more than one measurement on the same target, or when it is desired to make different measurements on several targets at locations across a substrate. Improved performance in metrology yields improved performance in the lithographic process, when corrections are applied based on measurement results obtained with the inspection apparatus.

A method of manufacturing devices using the lithographic process can be improved by providing an inspection apparatus as disclosed herein, using it to measure processed substrates to measure parameters of performance of the lithographic process, and adjusting parameters of the process to improve or maintain performance of the lithographic process for the processing of subsequent substrates.

Other advantages of the apparatuses and methods disclosed herein may include, but are not necessarily limited to, the following:

- in some examples, elimination of the need for a fiber split connection enables simplification of the system;
- in some examples, a single fiber connection to the source increases robustness of the system and means that fewer adjustments are required;
- in examples using reflective SLMs, e.g. those described above and shown in FIGS. 18 and 19, there are fewer optical losses, and therefore a higher light efficiency, since less light is absorbed in the system (e.g., a >2× improvement for examples where all pixels of the SLMs are in the 'on' state). Such an efficiency gain can be used to increase the spot size for the same source input power, or else the spot size can be maintained the same and the source input power reduced;
- there is no need or reduced need for mechanical shutters & aperture wheel, which means the system is less sensitive to vibrations & wear;
- there can be greater flexibility for pupil shape and polarization state;
- there are new options to calibrate and compensate for differences in an individual apparatus (e.g. polarization differences and system asymmetry);
- in small-target diffraction based overlay/focus/dose metrology, a strongly reduced sensitivity to process variations (by eliminating sensor asymmetry);
- reduced ghost light levels in the system (by optimizing pupil distribution);
- pupil and polarization can be optimized for optimum stack sensitivity; and
- the grating asymmetry impact can be estimated and the system can be optimized for smallest impact.

It should be understood that the particular parameters used in the above examples are not the only ones that may be defined. Additional and/or alternative parameters can be used in a real design process, according to limitations of the lithographic apparatus and the inspection apparatus to be used for the metrology. While the target structures described above are metrology targets specifically designed and formed for the purposes of measurement, in other embodiments, properties may be measured on targets which are functional parts of devices formed on the substrate. Many devices have regular, grating-like structures. The terms 'target grating' and 'target structure' as used herein do not require that the structure has been provided specifically for the measurement being performed.

In association with the physical grating structures of the targets as realized on substrates and patterning devices, an embodiment may include a computer program containing one or more sequences of machine-readable instructions describing a methods of designing metrology recipes and/or controlling the inspection apparatus to implement the illumination modes and other aspects of those metrology recipes. This computer program may be executed for example in a separate computer system employed for the design/control process. Alternatively, the design process may be wholly or partly performed within unit PU in the apparatus of FIG. 3, 4 or 5 and/or the control unit LACU of FIG. 2. There may also be provided a data storage medium (e.g., semiconductor memory, magnetic or optical disk) having such a computer program stored therein.

Although specific reference may have been made above to the use of embodiments of the invention in the context of optical lithography, it will be appreciated that the invention may be used in other applications, for example imprint lithography, and where the context allows, is not limited to optical lithography. In imprint lithography a topography in a patterning device defines the pattern created on a substrate.

The topography of the patterning device may be pressed into a layer of resist supplied to the substrate whereupon the resist is cured by applying electromagnetic radiation, heat, pressure or a combination thereof. The patterning device is moved out of the resist leaving a pattern in it after the resist is cured.

Further embodiments according to the invention are provided in below numbered clauses:

1. An illumination system for conditioning a beam of radiation in an illumination path of an optical system, the illumination system comprising:
   a beam combiner having a first input path, a second input path and an output path,
   a first spatial light modulator for receiving first radiation and spatially modulating the first radiation in accordance with a first programmable pattern;
   a second spatial light modulator for receiving second radiation and spatially modulating the second radiation in accordance with a second programmable pattern; and
   one or more polarizing elements,
   wherein the beam combiner is configured to receive the spatially modulated first radiation via said first input path, to receive the spatially modulated second radiation via said second input path and to output spatially modulated combined radiation via said output path;
   and wherein the polarizing elements, the spatial light modulators and the beam combiner are configured such that the combined radiation has a first polarized component in portions of the output path determined by the first programmable pattern and has a second polarized component in portions of the output path determined by the second programmable pattern.

2. An illumination system according to clause 1 wherein said first polarized component comprises radiation polarized linearly with a first polarization direction and the second polarized component comprises radiation polarized linearly with a second polarization direction.

3. An illumination system according to clause 1 or 2 wherein, depending on the first programmable pattern and the second programmable pattern, a portion of the output path may be given (i) substantially no radiation, (ii) radiation comprising substantially only the first polarized component, (iii) radiation comprising substantially only the second polarized component and (iv) radiation comprising both the first and second polarized components.

4. An illumination system according to clause 1, 2 or 3 wherein the first programmable pattern can set to select between more than two levels of radiation of the first polarized component.

5. An illumination system according to any preceding clause wherein the first spatial light modulator is configured to vary a polarization state of the first radiation in portions of the first input path determined by the first programmable pattern.

6. An illumination system according to clause 5 wherein the beam combiner comprises a polarizing beam splitter, the polarizing beam splitter selectively delivering the spatially modulated first radiation from the first input path of the beam combiner to the output path, depending on the polarization state of the spatially modulated first radiation.

7. An illumination system according to clause 5 or 6 wherein said polarizing elements include a first pre-polarizer for applying polarization to the first radiation prior to the first spatial light modulator.

8. An illumination system according to clause 5, 6 or 7 wherein said polarizing elements include a first analyzer for selectively transmitting the spatially modulated first radiation to the first input path of the beam combiner, depending on the polarization state of the spatially modulated first radiation.

9. An illumination system according to any preceding clause wherein the first programmable pattern can set to select between more than two levels of radiation of the second polarized component.

10. An illumination system according to any preceding clause wherein the second spatial light modulator is configured to vary a polarization state of the second radiation in portions of the second input path determined by the second programmable pattern.

11. An illumination system according to clause 10 wherein the beam combiner comprises a polarizing beam splitter, the polarizing beam splitter selectively delivering the spatially modulated second radiation from the second input path of the beam combiner to the output path, depending on the polarization state of the spatially modulated second radiation.

12. An illumination system according to clause 10 or 11 wherein said polarizing elements include a second pre-polarizer for applying polarization to the second radiation prior to the second spatial light modulator.

13. An illumination system according to clause 10, 11 or 12 wherein said polarizing elements include a second analyzer for selectively transmitting the spatially modulated second radiation to the second input path of the beam combiner, depending on the polarization state of the spatially modulated second radiation.

14. An illumination system according to any of clauses 1 to 4 wherein:
   the beam combiner comprises a polarizing beam splitter, the polarizing beam splitter selectively transmitting the spatially modulated first radiation from the first input path of the beam combiner to the output path, depending on the polarization state of the spatially modulated first radiation;
   said polarizing elements include a first pre-polarizer for applying polarization to the first radiation prior to the first spatial light modulator; and
   the polarizing beam splitter is arranged to serve simultaneously as the first pre-polarizer and the beam combiner.

15. An illumination system according to clause 14 wherein:
   the polarizing beam splitter is further configured to selectively deliver the second radiation from the second input path of the beam combiner to the output path, depending on the polarization state of the spatially modulated second radiation;
   the polarizing elements include a second pre-polarizer for applying polarization to the second radiation prior to the second spatial light modulator; and
   the polarizing beam splitter is arranged to serve simultaneously as the first pre-polarizer, the second pre-polarizer and the beam combiner.

16. An illumination system according to clause 14 or 15 wherein the first spatial light modulator is configured to vary a polarization state of the first radiation in portions of the first input path determined by the first programmable pattern.

17. An illumination system according to any of clauses 14, 15 or 16 wherein the second spatial light modulator is configured to vary a polarization state of the second radiation in portions of the second input path determined by the second programmable pattern.

18. An illumination system according to clause 14 or 15 wherein:

the first spatial light modulator comprises a plurality of reflective elements configured to reflect the first radiation in portions of the first input path determined by the first programmable pattern; and an element is arranged between the polarizing beam splitter and the first spatial light modulator to vary a polarization of the first radiation prior to the first spatial modulator and to vary a polarization of the first spatially modulated radiation.

19. An illumination system according to clause 14, 15 or 18 wherein:

the second spatial light modulator comprises a plurality of reflective elements configured to reflect the second radiation in portions of the second input path determined by the second programmable pattern; and an element is arranged between the polarizing beam splitter and the second spatial light modulator to vary a polarization of the second radiation prior to the second spatial modulator and to vary a polarization of the second spatially modulated radiation.

20. An illumination system according to any of clauses 14 to 19, wherein the polarizing beam splitter includes a partially reflecting surface, the partially reflecting surface being configured simultaneously (i) to pre-polarize the first radiation by transmission through the partially reflecting surface, (ii) to deliver the spatially modulated first radiation to the output path by reflection from the partially reflecting surface, (iii) to pre-polarize the second radiation by reflection from the partially reflecting surface and (iv) to deliver the spatially modulated second radiation to the output path by transmission through the partially reflecting surface.

21. An illumination system according to any of clauses 5 to 20 wherein each of the first spatial light modulator and the second spatial light modulator comprises a liquid crystal cell having a plurality of active areas, each active area varying the polarization state of a portion of the radiation according to its spatial position in the first input path or second input path.

22. An illumination system according to clause 20 wherein each of said active areas is configured to rotate a polarization direction of radiation in its portion of the first input path or second input path by an angle dependent on a respective one of the first and second illumination profiles.

23. An illumination system according to any preceding clause wherein the first spatial light modulator and the second spatial light modulator are formed by first and second portions of a larger, planar spatial light modulator.

24. An illumination system according to any preceding clause wherein one or both of the first spatial light modulator and the second spatial light modulator is a transmissive spatial light modulator.

25. An illumination system according to any of clauses 1 to 23 wherein one or both of the first spatial light modulator and the second spatial light modulator is a reflective spatial light modulator.

26. An illumination system according to any preceding clause wherein one or both of the first spatial light modulator and the second spatial light modulator are configured to apply a non-binary modulation to the first radiation and second radiation.

27. An illumination system according to clause 26 configured to use the non-binary illumination profile to implement an apodization filter.

28. An illumination system according to any preceding clause wherein the first spatial light modulator is configured to modulate a color of the spatially modulated first radiation and/or the second spatial light modulator is configured to modulate a color of the spatially modulated second radiation.

29. An illumination system according to clause 28 wherein each of the first and second spatial modulators comprises an array of active areas and neighboring active areas within each array are provided with different color filters.

30. An illumination system according to any preceding clause further comprising a controller configured to apply control signals to the first and second spatial light modulators so as to define from time to time the first programmable pattern and the second programmable pattern.

31. An illumination system according to any preceding clause wherein the first radiation illuminates the first spatial light modulator as a collimated beam and the second radiation illuminates the first spatial light modulator as a collimated beam.

32. An inspection apparatus comprising:
a support for a substrate
an illumination system for illuminating one or more structures of interest formed the substrate with radiation having desired characteristics, and
a detection system for detecting radiation scattered by the substrate to obtain a measurement of a property of one or more structures of interest on the substrate,
wherein the illumination system comprises an illumination system according to any preceding clause and wherein the inspection apparatus further comprises a controller for controlling the first and second spatial light modulators to implement a measurement-specific first programmable pattern and second programmable pattern for each measurement in a series of different measurements.

33. An inspection apparatus according to clause 32 wherein the first and second spatial light modulators are located effectively in a pupil plane of the illumination system.

34. An inspection apparatus according to clause 32 wherein the first and second spatial light modulators are located effectively in a field plane of the illumination system.

35. A method of manufacturing devices wherein a device pattern is applied to a series of substrates using a lithographic process, the method including:
using an inspection apparatus according to clause 32, 33 or 34 to measure a property of at least one structure of interest formed on at least one of said substrates, and
controlling the lithographic process for later substrates in accordance with the measured property.

36. A computer program product comprising machine-readable instructions for causing a processor to control the first and second spatial light modulators in an inspection apparatus according to any of clauses 32 to 35, thereby to implement a plurality of illumination modes, each illumination mode defining a specific combination of first and second programmable patterns.

37. An illumination system for conditioning a beam of radiation in an inspection apparatus, the illumination system comprising at least a first spatial light modulator for imparting a programmable first illumination profile to first radiation in a first optical path and a second spatial light modulator for imparting a programmable second illumination profile to second radiation in a second optical path, the illumination system further being arranged to combine the first radiation and second radiation so as to superimpose the first and second illumination profiles in an illumination path of the inspection apparatus, wherein the first radiation delivered to the illumination path from the first spatial light modulator has a first characteristic and the second radiation delivered to the illumination path from the second spatial light modulator has a second characteristic, in addition to any differences in illumination profile.

38. A illumination system according to clause 37 wherein said first characteristic and second characteristic differ in polarization, such that polarization of radiation delivered at each point across the illumination path can be controlled by controlling the first and second spatial light modulators.

39. An illumination system according to clause 38 wherein one or both of said first optical path and said second optical path includes a polarizer for applying polarization to radiation prior to applying the relevant illumination profile.

40. An illumination system according to clause 38 or 39 wherein the first spatial light modulator is configured to vary a polarization state of the first radiation selectively in accordance with the first illumination profile.

41. An illumination system according to clause 40 further comprising a first analyzer for selectively transmitting the first radiation from the first spatial light modulator to the illumination path, depending on a polarization state of the first radiation.

42. An illumination system according to clause 41 wherein the second spatial light modulator is also configured to vary a polarization state of the second radiation selectively in accordance with the second illumination profile.

43. An illumination system according to clause 42 further comprising a second analyzer for selectively transmitting the second radiation from the second spatial light modulator to the illumination pupil, depending on a polarization state of the second radiation, the second radiation being transmitted with a polarization state different to that in which the first radiation is transmitted.

44. An illumination system according to clause 43 wherein the first and second analyzers are provided by a polarizing beam splitter device that is also configured to combine the first and second radiation for delivery to the illumination pupil.

45. An illumination system according to any of clauses 40 to 44 wherein each of the first spatial light modulator and the second spatial light modulator comprises a liquid crystal cell having a plurality of active areas.

46. An illumination system according to clause 45 wherein each of said active areas can be controlled in response to a control signal to rotate a polarization direction of radiation by an angle dependent on a respective one of the first and second illumination profiles.

47. An illumination system according to clause 37, 38 or 39 wherein one or both of the first spatial light modulator and the second spatial light modulator is a reflective spatial light modulator, for example a digital micromirror device.

48. An illumination system according to any of clauses 37 to 47 wherein the first spatial light modulator and the second spatial light modulator are configured to apply a non-binary illumination profile to the first radiation and second radiation.

49. An illumination system according to clause 48 wherein the non-binary illumination profile implements an apodization filter in the illumination pupil.

The terms "radiation" and "beam" used herein encompass all types of electromagnetic radiation, including ultraviolet (UV) radiation (e.g., having a wavelength of or about 365, 355, 248, 193, 157 or 126 nm) and extreme ultra-violet (EUV) radiation (e.g., having a wavelength in the range of 5-20 nm), as well as particle beams, such as ion beams or electron beams.

The term "lens", where the context allows, may refer to any one or combination of various types of optical components, including refractive, reflective, magnetic, electromagnetic and electrostatic optical components.

The foregoing description of the specific embodiments will so fully reveal the general nature of the invention that others can, by applying knowledge within the skill of the art, readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description by example, and not of limitation, such that the terminology or phraseology of the present specification is to be interpreted by the skilled artisan in light of the teachings and guidance.

The breadth and scope of the present invention should not be limited by any of the above-described exemplary embodiments, but should be defined only in accordance with the following claims and their equivalents.

The invention claimed is:

1. An illumination system comprising:
   a beam combiner having a first input path, a second input path and an output path,
   a first spatial light modulator configured to receive and spatially modulate first radiation in accordance with a first programmable pattern;
   a second spatial light modulator configured to receive and spatially modulate second radiation in accordance with a second programmable pattern; and
   a polarizing element configured to polarize both the first radiation and the second radiation in a single polarization direction for input into the first spatial light modulator and second spatial light modulator, respectively;
   wherein the beam combiner is configured to receive the spatially modulated first radiation via said first input path, to receive the spatially modulated second radiation via said second input path and to output spatially modulated combined radiation via said output path; and
   wherein the polarizing element, the spatial light modulators and the beam combiner are configured such that the combined radiation has a first polarized component in portions of the output path determined by the first programmable pattern and has a second polarized component in portions of the output path determined by the second programmable pattern.

2. The illumination system as claimed in claim 1, wherein said first polarized component comprises radiation polarized linearly with a first polarization direction and the second polarized component comprises radiation polarized linearly with a second polarization direction different from the first polarization direction.

3. The illumination system as claimed in claim 1, wherein depending on the first programmable pattern and the second programmable pattern, a portion of the output path may be given substantially no radiation, radiation comprising substantially only the first polarized component, radiation comprising substantially only the second polarized component, or radiation comprising both the first and second polarized components.

4. The illumination system as claimed in claim 1, wherein the first programmable pattern can set to select between more than two levels of radiation of the first polarized component.

5. The illumination system as claimed in claim 1, wherein the first spatial light modulator is configured to vary a polarization state of the first radiation in portions of the first input path determined by the first programmable pattern.

6. The illumination system as claimed in claim 5, wherein the beam combiner comprises a polarizing beam splitter, the polarizing beam splitter selectively delivering the spatially modulated first radiation from the first input path of the beam combiner to the output path, depending on the polarization state of the spatially modulated first radiation.

7. The illumination system as claimed in claim 5, wherein each of the first spatial light modulator and the second spatial light modulator comprises a liquid crystal cell having a plurality of active areas, each active area varying the polarization state of a portion of the radiation according to its spatial position in the first input path or second input path.

8. The illumination system as claimed in claim 7, wherein each of said active areas is configured to rotate a polarization direction of radiation in its portion of the first input path or second input path by an angle dependent on a respective one of the first and second programmable patterns.

9. The illumination system as claimed in claim 1, wherein one or both of the first spatial light modulator and the second spatial light modulator is a transmissive spatial light modulator.

10. The illumination system as claimed in claim 1, wherein one or both of the first spatial light modulator and the second spatial light modulator are configured to apply a non-binary modulation to the first radiation and second radiation.

11. The illumination system as claimed in claim 1, wherein the first spatial light modulator is configured to modulate a color of the spatially modulated first radiation and/or the second spatial light modulator is configured to modulate a color of the spatially modulated second radiation.

12. The illumination system as claimed in claim 1, wherein the first polarized component comprises radiation polarized linearly with a first polarization direction and the second polarized component comprises radiation polarized linearly with a second polarization direction different from the first polarization direction.

13. The illumination system as claimed in claim 1, wherein the first programmable pattern can set to select between more than two levels of radiation of the first polarized component.

14. The illumination system as claimed in claim 1, wherein the first spatial light modulator is configured to vary a polarization state of the first radiation in portions of the first input path determined by the first programmable pattern.

15. The illumination system as claimed in claim 14, wherein the beam combiner comprises a plurality of polarizing beam splitters, the polarizing beam splitters selectively delivering the spatially modulated first radiation from the first input path of the beam combiner to the output path, depending on the polarization state of the spatially modulated first radiation.

16. The illumination system as claimed in claim 14, wherein each of the first spatial light modulator and the second spatial light modulator comprises a liquid crystal cell having a plurality of active areas, each active area varying the polarization state of a portion of the radiation according to its spatial position in the first input path or second input path.

17. The illumination system as claimed in claim 16, wherein each of the active areas is configured to rotate a polarization direction of radiation in its portion of the first input path or second input path by an angle dependent on a respective one of the first and second programmable patterns.

18. An inspection apparatus comprising:
a support for a substrate;
an illumination system configured to illuminate one or more structures of interest formed on the substrate with radiation having desired characteristics, and
a detection system for detecting radiation scattered by the substrate to obtain a measurement of a property of the one or more structures of interest on the substrate,
wherein the illumination system comprises:
a beam combiner having a first input path, a second input path and an output path,
a first spatial light modulator configured to receive and spatially modulate the first radiation in accordance with a first programmable pattern;
a second spatial light modulator configured to receive and spatially modulate the second radiation in accordance with a second programmable pattern; and
a polarizing element configured to polarize both the first radiation and the second radiation in a single polarization direction for input into the first spatial light modulator and second spatial light modulator, respectively;
wherein the beam combiner is configured to receive the spatially modulated first radiation via said first input path, to receive the spatially modulated second radiation via said second input path and to output spatially modulated combined radiation via said output path; and
wherein the polarizing element, the spatial light modulators and the beam combiner are configured such that the combined radiation has a first polarized component in portions of the output path determined by the first programmable pattern and has a second polarized component in portions of the output path determined by the second programmable pattern, and
wherein the inspection apparatus further comprises a controller for controlling the first and second spatial light modulators to implement a measurement-specific first programmable pattern and second programmable pattern for each measurement in a series of different measurements.

19. The illumination system as claimed in claim 18, wherein one or both of the first spatial light modulator and the second spatial light modulator are configured to apply a non-binary modulation to the first radiation and second radiation.

20. The illumination system as claimed in claim 18, wherein the first spatial light modulator is configured to modulate a color of the spatially modulated first radiation and/or the second spatial light modulator is configured to modulate a color of the spatially modulated second radiation.

* * * * *